United States Patent
Heller et al.

(10) Patent No.: US 10,792,375 B2
(45) Date of Patent: *Oct. 6, 2020

(54) METHOD FOR THE TREATMENT OF MALIGNANCIES

(71) Applicant: University of South Florida, Tampa, FL (US)

(72) Inventors: Richard Heller, Norfolk, VA (US); Kenneth E. Ugen, Tampa, FL (US)

(73) Assignee: University of South Florida, Tampa, FL (US)

( * ) Notice: Subject to any disclaimer, the term of this patent is extended or adjusted under 35 U.S.C. 154(b) by 60 days.

This patent is subject to a terminal disclaimer.

(21) Appl. No.: 16/208,144

(22) Filed: Dec. 3, 2018

(65) Prior Publication Data
US 2019/0105408 A1    Apr. 11, 2019

Related U.S. Application Data

(60) Continuation of application No. 15/477,783, filed on Apr. 3, 2017, now Pat. No. 10,143,759, which is a continuation of application No. 14/589,463, filed on Jan. 5, 2015, now Pat. No. 9,610,364, which is a continuation of application No. 13/969,078, filed on Aug. 16, 2013, now Pat. No. 8,927,518, which is a division of application No. 13/216,855, filed on Aug. 24, 2011, now Pat. No. 8,802,643, which is a continuation-in-part of application No. 11/164,626, filed on Nov. 30, 2005, now Pat. No. 8,026,223, which is a continuation of application No. PCT/US2004/017153, filed on Jun. 1, 2004.

(60) Provisional application No. 60/320,239, filed on May 30, 2003.

(51) Int. Cl.
| | |
|---|---|
| *A61K 48/00* | (2006.01) |
| *A61K 35/17* | (2015.01) |
| *A61K 38/20* | (2006.01) |
| *C12N 15/85* | (2006.01) |
| *C07K 14/705* | (2006.01) |
| *A61N 1/32* | (2006.01) |
| *A61K 38/00* | (2006.01) |

(52) U.S. Cl.
CPC .......... *A61K 48/005* (2013.01); *A61K 35/17* (2013.01); *A61K 38/2086* (2013.01); *A61K 48/0083* (2013.01); *A61N 1/327* (2013.01); *C07K 14/70532* (2013.01); *A61K 38/00* (2013.01)

(58) Field of Classification Search
None
See application file for complete search history.

(56) References Cited

U.S. PATENT DOCUMENTS

| | | |
|---|---|---|
| 6,593,130 B1 | 7/2003 | Sen et al. |
| 6,697,669 B2 | 2/2004 | Dev et al. |
| 6,972,013 B1 | 12/2005 | Zhang et al. |
| 7,323,450 B2 | 1/2008 | Chu et al. |
| 7,412,284 B2 | 8/2008 | Hofmann |
| 8,026,223 B1 | 9/2011 | Heller et al. |
| 8,802,643 B1 | 8/2014 | Heller et al. |
| 8,927,518 B1 | 1/2015 | Heller et al. |
| 9,610,364 B1 | 4/2017 | Heller et al. |
| 10,143,759 B1 * | 12/2018 | Heller ............... A61K 48/0083 |
| 2003/0018006 A1 | 1/2003 | Tao et al. |

FOREIGN PATENT DOCUMENTS

WO    2004110371 A2    12/2004

OTHER PUBLICATIONS

Chen, et al. (1997) "Eradication of murine bladder carcinoma by intratumor injection of a bicistronic adenoviral vector carrying cDNAs for the IL-12 heterodimer and its inhibition by the IL-12 p40 subunit homodimer", The Journal of Immunology, 159: 351-59. (Year: 1997).*

Waldmann, et al. (1999) "The multifaceted regulation of Interleukin-15 expression and the role of this cytokine in NK cell differentiation and host response to intracellular pathogens", Annual Review of Immunology, 17: 17-49. (Year: 1999).*

Andre et al., DNA Electrotransfer: Its Principles and an Updated Review of Its Therapeutic Applications, Gene Therapy, 2004, vol. 11, pp. S33-S42.

Heller et al., Clinical Applications of Electrochemotherapy, Advanced Drug Delivery Reviews, 1999, vol. 35, pp. 119-129.

Heller et al., In Vivo Electroporation of Plasmids Encoding GM-CSF or Interleukin-2 into Existing B16 Melanomas mbined with Electrochemotherapy Induces Long-term Antiturnor Immunity, Melanoma Research, 2000, vol. 10, pp. 577-583.

(Continued)

*Primary Examiner* — Robert M Kelly
(74) *Attorney, Agent, or Firm* — Meunier Carlin & Curfman LLC

(57) ABSTRACT

A method of treating cancerous tumors is presented herein. The method includes injecting an effective dose of a plasmid encoded for IL-12, B7-1 or IL-15 into a cancerous tumor and subsequently administering at least one high voltage, short duration pulse to the tumor. The electroporation pulses may be administered at al least 700 V/cm for a duration of less than 1 millisecond. The intratumor treatments with electroporation may be administered in at least a two-treatment protocol with the time between treatments being about 7 days. The intratumor treatments with electroporation may be administered in a three-treatment protocol with a time of four days between the first and second treatments and a time of three days between the second and third treatments. It was found that the intratumor treatments using electroporation not only resulted in tumor regression but also induced an immune memory response which prevented the formation of new tumors.

21 Claims, 23 Drawing Sheets

(56) References Cited

OTHER PUBLICATIONS

International Search Report for International application No. PCT/US04/17153 dated Jan. 7, 2005.

Kishida et al., Electrochemo-Gene Therapy of Cancer: Intratumoral Delivery of Interleukin-12 Gene and Bleomycin Synergistically Induced Therapeutic Immunity and Suppressed Subcutaneous and Metastatic Melanomas in Mice, Molecular Therpay, 2003, vol. 8, No. 5, pp. 738-745.

Lee et al., Inhibition of Established Subcutaneous and Metastatic Murine Tumors by Intramuscular Electroporation of the Interleukin-12 Gene, Journal of Biomedical Science, 2003, vol. 10, pp. 73-86.

Liu, et al. (2006) "The mechanism of exogenous B7.1-enhanced IL-12-mediated complete regression of tumors by a single electroporation delivery", International Journal of Cancer, 119: 2113-18.

Lohr et al., Effective Tumor Therapy with Plasmid-Encoded Cytokines Combined with in Vivo Electroporation, Cancer Research, 2001, vol. 61, pp. 3281-3284.

Lucas et al., IL-12 Gene Therapy Using an Electrically Mediated Nonviral Approach Reduces Metastatic Growth of Melanoma, DNA and Cell Biology, 2003, vol. 22, No. 12, pp. 755-763.

Lucas et al., IL-12 Plasmid Delivery by in Vivo Electroporation for the Successful Treatment of Established Subcutaneous B16.F10 Melanoma, Molecular Therapy, 2002, vol. 5, No. 6. pp. 668-675.

Miklavcic, et al. (2004) Electroporation for electrochemotherapy and gene therapy. In: P.J. Rosch and M.S. Markov, Editors, Bioelectromagnetic Medicine, Marcel Dekker, New York, pp. 637-656.

Mir et al., High-Efficiency Gene Transfer into Skeletal Muscle Mediated by Electric Pulses, PNAS, 1999, vol. 96, No. 8, p. 4262-4267.

Rols, et al. (1998) "In vivo electrically mediated protein and gene transfer in murine melanoma", Nature Biotechnology: 6(2):168-71.

Yamashita et al., Electroporation-Mediated Interleukin-12 Gene Therapy for Hepatocellular Carcinoma in the Mice Model. Cancer Research, 2001, vol. 61, pp. 1005-1012.

* cited by examiner

TABLE 1: Tumor blood vessel counts from C57BL/6 mice in each treatment group

|  | P-E- | P-E- i.t. | P-E- i.m. | V+E+ i.t. | P+E+ i.m. | P+E+ i.t. |
|---|---|---|---|---|---|---|
| Tumor 1 | 24 | 10 | 27 | 20 | 17 | 6 |
| Tumor 2 | 32 | 21 | 32 | 28 | 38 | 12 |
| Tumor 3 | 49 | 28 | 39 | 39 | 38 | 18 |

P-, No plasmid; E-, no electroporation; P+, pIRES IL-12; E+, electroporation; V+, control plasmid, pND2Lux; i.t., intratumoral; i.m., intramuscular.

FIG. 7

|  | P-E- | V+E+ | P+E- | P+E+ |
|---|---|---|---|---|
| Number of lung tumor nodules in each mouse per treatment group. | 0 | 0 | 0 | 0 |
|  | 3 | 0 | 0 | 0 |
|  | 8 | 4 | 2 | 0 |
|  | 10 | 4 | 3 | 0 |
|  | 16 | 13 | 6 | 0 |
|  | 32 | 14 | 20 | 1 |
|  | 45 | 18 | 30 | 1 |
|  | 50 | 35 | 40 | 40 |

*FIG. 11*

| Group | Day 0 TV$^a$ (mm) | Day 18 TV$^a$ (mm) | Fold increase in TV$^a$ (D0- D18) | Day 18 % R$^b$ |
|---|---|---|---|---|
| P-V-E- | 46.5 | 1026.8 | 12.1 | 0 |
| P-V+E- | 39.4 | 479.9 | 12.1 | 0 |
| P-V+E+ | 40.0 | 166.8 | 4.2 | 6.25 |
| P+V-E- | 36.2 | 564.2 | 15.6 | 18.75 |
| P+V-E+ | 39.9 | 49.6 | 1.2 | 62.5 |

$^a$ TV = Tumor volume.

$^b$ %R = Percent of mice with complete tumor regression.

FIG. 15

METHOD FOR THE TREATMENT OF MALIGNANCIES

CROSS REFERENCE TO RELATED APPLICATIONS

This application is a continuation of and claims the benefit of U.S. application Ser. No. 15/477,783, entitled "Method for the Treatment of Malignancies", filed Apr. 3, 2017, now U.S. Pat. No. 10,143,759, which is a continuation of and claims the benefit of U.S. application Ser. No. 14/589,463, entitled "Method for the Treatment of Malignancies", filed Jan. 5, 2015, now U.S. Pat. No. 9,610,364, which is a continuation of and claims the benefit of U.S. Pat. No. 8,927,518, entitled "Method for the Treatment of Malignancies", filed Aug. 16, 2013, which is a divisional of and claims the benefit of U.S. Pat. No. 8,802,643, entitled "Method for the Treatment of Malignancies", filed on Aug. 24, 2011, which is a continuation in part of and claims the benefit of U.S. Pat. No. 8,026,223, entitled "Method for the Treatment of Malignancies", filed Nov. 30, 2005, which claims the benefit of International Patent Application No. PCT/US2004/017153, entitled "Method for the Treatment of Malignancies", filed Jun. 1, 2004, which claims the benefit of U.S. Provisional Patent Application No. 60/320,239, entitled "IL-12 Plasmid Delivery by In Vivo Electroporation for the Successful Treatment of Established Subcutaneous B16.F10 Melanoma", filed May 30, 2003, the contents of each of which are hereby incorporated by reference.

GOVERNMENTAL SUPPORT

This invention was made with government support under Grant Number ROI CA122518 awarded by the National Institutes of Health. The government has certain rights in the invention.

BACKGROUND OF INVENTION

The effective treatment of metastases is a challenge for any cancer treatment. For immunotherapy to be beneficial in the treatment of metastatic disease, the immune system must recognize tumor cells throughout the body, which can be achieved by inducing a systemic immune response or through the creation of memory T cells following recognition of a primary tumor.

Many cytokines have been intensively investigated as potential anticancer agents. Among the many cytokines evaluated, Interleukin-12 (IL-12) has been shown to exhibit strong antitumor activities. IL-12 can upregulate the proliferation and maturation of T cells and natural killer (NK) cells, induce production of IFN-γ, inhibit angiogenesis, and upregulate expression of accessory molecules such as HLA. Unfortunately, delivery of IL-12 in the form of recombinant protein results in severe toxicity and adverse side effects, including death. Therefore, gene therapy strategies for delivery of IL-12 have been explored such as the use of viral vectors, gene gun, microspheres, direct injection of plasmid, and electroporation.

The antitumor potential of IL-12 has been reported in numerous immunotherapy studies. The proposed antitumor mechanisms of IL-12 include effects on the immune system such as the induction of IFN-γ, upregulation of T cells, and proliferation of natural killer (NK) cells. In addition, IL-12 inhibits angiogenesis, the formation of new blood vessels. This wide range of effects on the immune system as well as antiangiogenic properties results in a potentially potent antitumor treatment. Unfortunately, preclinical and clinical trials using systemic administration of recombinant IL-12 demonstrated potential adverse side effects. Administration of recombinant IL-12 locally or systemically has been reported to induce potent antitumor activity in a variety of murine tumor models, causing regression of established tumors. However, in these studies, repeated delivery of recombinant IL-12 on a daily basis was required to achieve the maximal therapeutic activity, and was also usually associated with a dose-dependent toxicity. The use of gene therapy for the delivery of IL-12, by gene gun, resulted in fewer side effects than recombinant protein therapy. Several studies using viral and nonviral gene delivery techniques have reported success in slowing and/or preventing tumor growth. However, these studies have had limited success in demonstrating complete regression of the poorly immunogenic B16.F10 melanoma and subsequent resistance to challenge.

In vivo electroporation is a gene delivery technique that has been used successfully for efficient delivery of plasmid DNA to many different tissues. Studies have reported the administration of in vivo electroporation for delivery of plasmid DNA to B16 melanomas and other tumor tissues. Although systemic administration of recombinant IL-12 revealed its antitumor potential, expression of IFN-gamma at the tumor site has been shown to be critical for successful tumor regression. Systemic and local expression of a gene or cDNA encoded by a plasmid can be obtained with administration of in vivo electroporation. Use of in vivo electroporation enhances plasmid DNA uptake in tumor tissue, resulting in expression within the tumor, and delivers plasmids to muscle tissue, resulting in systemic cytokine expression.

It has been shown that electroporation can be used to transfect cells in vivo with plasmid DNA. Recent studies have shown that electroporation is capable of enhancing delivery of plasmid DNA as an antitumor agent. Electroporation has been administered for treatment of hepatocellular carcinomas, adenocarcinoma, breast tumors, squamous cell carcinoma and B16.F10 melanoma in rodent models. The B16.F10 murine melanoma model has been used extensively for testing potential immunotherapy protocols for the delivery of IL-12 and other cytokines either as recombinant protein or by gene therapy.

Its wide range of effects on the immune system and its antiangiogenic properties make IL-12 an excellent candidate for use an as immunotherapeutic agent. Because of its potential toxicity, it is important to give careful consideration to the delivery method of IL-12. In vivo electroporation is a safe, nontoxic delivery system and has been used for efficient delivery of chemotherapeutic agents and plasmid DNA, including plasmids encoding IL-12.

Electroporation mediated in vivo delivery of the murine interleukin-12 (IL-12) gene in an expression plasmid has been shown to provide antitumor and antimetastasis activity. Various protocols are known in the art for the delivery of plasmid encoding IL-12 utilizing in vivo electroporation for the treatment of cancer. The protocols known in the art describe in vivo electroporation mediated cytokine based gene therapy, both intratumor and intramuscular, utilizing low-voltage and long-pulse currents. Prior art methods have identified these low-voltage levels to be less than 300V and long pulses to be in the area of 50 ms. Rationalization for the use of low-voltage levels and long pulse lengths for the delivery of plasmid encoding IL-12 for the treatment of tumors is based on well-known principles of electroporation and electrochemotherapy. It is known that electric pulses with moderate electric field intensity can cause temporary cell membrane permeabilization, which may then lead to rapid genetic transformation and manipulation in a wide variety of cells types including bacteria, yeasts, animal and human cells, and so forth. Conversely, electric pulses with high electric field intensity can cause permanent cell membrane breakdown and tissue damage. All prior art methods describing the administration of an electroporation protocol for delivery of IL-12 to the target tissue are based on the application of low-voltage, long length pulses. These treatment protocols known in the art have not been effective in demonstrating acceptable cure rates for tumors, including B16.F10 melanoma tumors. Additionally, the known treatment protocols have been unable to demonstrate improved long-term subject survival rates.

Accordingly, what is needed in the art is an electroporation protocol for the delivery of a plasmid encoding a therapeutic protein that will provide substantially improved results in the regression of cancer tumors while also substantially improving the long-term survival rates.

SUMMARY OF INVENTION

The present invention provides a method for the treatment of malignancies, wherein the administration of a plasmid encoding for a therapeutic protein in combination with electroporation has a therapeutic effect on primary tumors as well as distant tumors and metastases.

According to one embodiment of the invention, a method of treating a subject having a cancerous tumor is provided, the method includes injecting the cancerous tumor with an effective dose of plasmid coding for a therapeutic protein and administering electroporation therapy to the tumor. The electroporation therapy further includes the administration of at least one high voltage pulse having a short duration.

The method of the present invention is effective in the treatment of a variety of cancerous tumors, including melanoma. The data presented is an exemplary embodiment of the present invention for the treatment of B16.F10 melanoma in mice. However, the exemplary embodiment and data presented are not intended to limit the method of the present invention to the treatment of B16.F10 melanoma. The method of the present invention is applicable to the treatment of a variety of cancers, including, but not limited to melanoma, Merkel cell carcinoma, T-cell lymphoma, squamous cell carcinoma, pancreatic cancer, and hepatocellular carcinoma.

A variety of cytokines have been identified as being effective in the treatment of cancer. Interleukin 12 (IL-12) is a cytokine that has been studied extensively as an antitumor agent. In a particular embodiment of the present invention, the plasmid coding for a therapeutic protein administered to a subject is a plasmid coding for IL-12.

In an additional embodiment, the plasmid coding for a therapeutic protein administered to a subject is a plasmid coding for B7-1.

In an additional embodiment, the plasmid coding for a therapeutic protein administered to a subject is a plasmid coding for IL-15.

Other effective cytokines are within the scope of the present invention.

The electroporation therapy administered in accordance with the present invention is characterized by high voltages pulses of short duration. In accordance with the present invention, a high voltage pulse is defined to be greater than about 400 V/cm. Additionally, in accordance with the present invention a short duration pulse is defined to be less than about 1 millisecond.

In a particular embodiment, the electroporation therapy administered to the subject tumor includes at least one high voltage pulse of about 1500 V/cm having a duration of about 100 microseconds.

In an additional embodiment, the method of the present invention further includes the step of injecting an effective dose of plasmid encoding for a therapeutic protein into the muscle tissue of the subject and administering electroporation to the subject intramuscularly using at least one low voltage pulse having a long pulse width. The plasmid encoding for a therapeutic protein used in this step may be a plasmid encoding for IL-12, or any other effective plasmid.

In a particular embodiment of the intramuscular electroporation therapy step, the voltage level is a voltage of about 100 V/cm and the pulse duration is about 20 milliseconds.

An increase in the effectiveness of the treatment has been observed when the treatment method of the present invention is administered multiple times. In this instance, a method of treating a subject having a cancerous tumor, is provided which includes injecting the cancerous tumor with a first effective dose of plasmid coding for a therapeutic protein, administering a first electroporation therapy to the tumor, the first electroporation therapy further comprising the administration of at least one high voltage pulse having a short duration, then subsequently injecting the cancerous tumor with a second effective dose of plasmid coding for a therapeutic protein, and administering a second electroporation therapy to the tumor, the second electroporation therapy further comprising the administration of at least one high voltage pulse having a short duration. Additionally, a third effective dose of plasmid coding for a therapeutic protein and a third electroporation therapy may be administered to the tumor, the third electroporation therapy further comprising the administration of at least one high voltage pulse having a short duration. This two or three step process may be followed by the step of injecting an effective dose of plasmid encoding for a therapeutic protein into the muscle tissue of the subject and administering electroporation to the subject intramuscularly using at least one low voltage pulse having a long pulse width.

A plurality of high voltage, short pulse duration electroporation therapy conditions are within the scope of the present invention. In an exemplary embodiment, the method of the present invention includes injecting a cancerous tumor with a first effective dose of plasmid coding for IL-12, administering a first electroporation therapy to the tumor, the first electroporation therapy further comprising the administration of six pulses delivered at 1500 V/cm at 100 microseconds pulse duration, injecting the cancerous tumor with a second effective dose of plasmid coding for IL-12, administering a second electroporation therapy to the tumor, the second electroporation therapy further comprising the administration of six pulses delivered at 1500 V/cm at 100 microseconds pulse duration, injecting the cancerous tumor with a third effective dose of plasmid coding IL-12, and administering a third electroporation therapy to the tumor, the third electroporation therapy further comprising the administration of six pulses delivered at 1500 V/cm at 100 microseconds pulse duration. Additionally, the method may include injecting an effective dose of plasmid encoding for a therapeutic protein into the muscle tissue of the subject, administering electroporation to the subject intramuscularly using 12 pulses delivered at 100 V/cm of 20 milliseconds in duration.

In an exemplary embodiment of the present invention, a method for the treatment of malignancies is provided wherein the method includes administering a first treatment on day zero, the first treatment comprising injecting the cancerous tumor with a first effective dose of plasmid coding for IL-12 and administering a first electroporation therapy to the tumor, the first electroporation therapy further comprising the administration of six pulses delivered at 1500 V/cm at 100 microseconds pulse duration. On day four a second treatment is administered comprising injecting the cancerous tumor with a second effective dose of plasmid coding for IL-12 and administering a second electroporation therapy to the tumor, the second electroporation therapy further comprising the administration of six pulses delivered at 1500 V/cm at 100 microseconds pulse duration. On day seven a third treatment is administered, the third treatment comprising injecting the cancerous tumor with a third effective dose of plasmid coding IL-12 and administering a third electroporation therapy to the tumor, the third electroporation therapy further comprising the administration of six pulses delivered at 1500 V/cm at 100 microseconds pulse duration. An additional step may include injecting an effective dose of plasmid encoding for IL-12 into the muscle tissue of the subject, administering electroporation therapy to the subject intramuscularly using twelve pulses delivered at 100 V/cm at 20 millisecond duration.

In an additional embodiment, delivery of plasmid encoding B7-1 to melanoma tumors utilizes 1300 V/cm pulses of 100 μs in duration.

In an additional embodiment, Interleukin-15 (IL-15) is delivered intratumorally utilizing electroporation. IL-15 is a 15 kDa cytokine protein that uses the gamma and beta chains of the IL-2 receptor complex with a unique alpha chain to signal T cells. It stimulates memory CD8+ cells in contrast to IL-2, which inhibits memory CD8+ T-cell proliferation. In addition, IL-15 also inhibits IL-2-mediated activation-induced cell death (AICD) associated with self-tolerance. Likewise, in addition to stimulating memory CD8+ T cells, IL-15 also stimulates the activation, proliferation and cytotoxicity of natural killer (NK) cells. As such, IL-15 has been targeted as an antitumor cytokine with potential advantages over IL-2.

In the present invention, IL-15 was delivered as a DNA plasmid through electroporation to mediate antitumor activity. In a particular embodiment, the cancerous tumor was injected with an effective dose of plasmid coding for IL-15 and electroporation therapy was delivered to the tumor, the electroporation therapy comprising the administration of at least one pulse having a field strength of at least 700 V/cm and a duration of less than 1 millisecond.

As demonstrated by the results provided in the detailed description, the method of the present invention provides a treatment protocol for cancer resulting in a statistically significant improvement in survival rates over all other known methods in the art that utilize a plasmid coding for IL-12, IL-15 or B7-1 and electroporation. The protocol of the present invention utilizes high voltage, short duration pulses. All other protocols known in the art for the delivery and expression of IL-12, IL-15 or B7-1, utilize low voltage, long duration electroporation pulses. As such, the present invention results in new and unexpected results based on a novel protocol for the delivery of a plasmid coding for a protein and electroporation.

BRIEF DESCRIPTION OF THE DRAWINGS

For a fuller understanding of the nature and objects of the invention, reference should be made to the following detailed description, taken in connection with the accompanying drawings, in which:

FIG. 1B illustrated the percentage survival of mice represented in FIG. 1A. Mice either succumbed to disease or were killed when tumor volume exceeded 1000 mm3.

FIG. 5B illustrates percentage survival of mice represented in FIG. 5A. Mice either succumbed to disease or were killed when tumor volume exceeded 1000 mm3.

FIG. 7 is a table illustrating the tumor blood vessel counts from C57BL/6 mice in each treatment group.

FIG. 8B depicts percent survival of nice following treatment. Results represent the combined date of three replicate experiments and error bars represent the standard error of the mean. The total number of samples for each treatment group was 50. Mice were euthanized when tumor volume exceeded 1000 mm$^3$. Data is expressed for surviving mice on each day. P=pIRES IL-12; V=control plasmid, pND2Lux; E=electroporation. For location of treatment, i.t.=intratumor delivery; i.m.=intramuscular delivery.

FIG. 11 is a table illustrating the results of a treatment with intramuscular administration of IL-12 by electroporation and how the treatment prevents development of tumor nodules in the lungs.

FIG. 15 is a table illustrating the initial effects of pIL-15 plus electroporation on tumor growth.

DETAILED DESCRIPTION

Figure 1A:
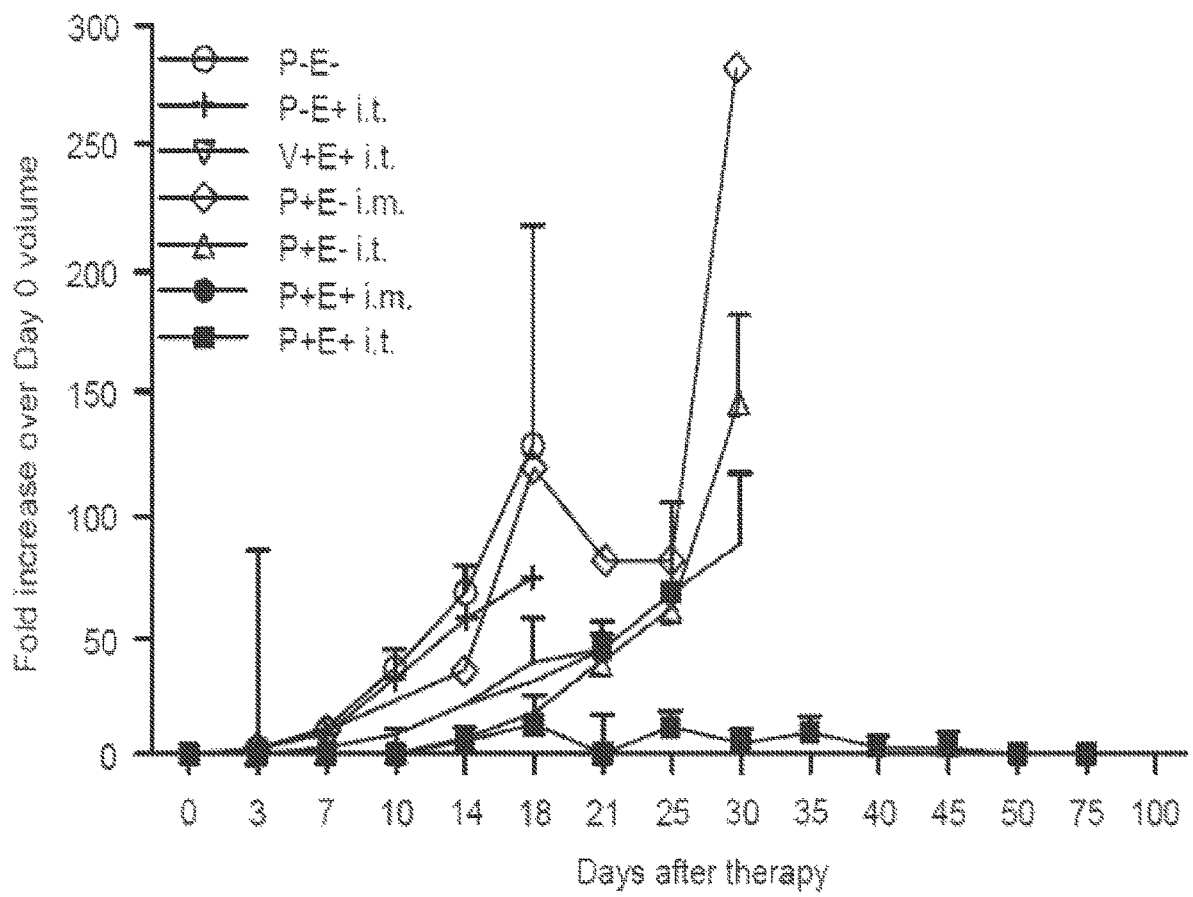
FIG. 1A is a graphical illustration of the administration of plasmid DNA encoding IL-12 followed by electroporation results in complete tumor regression. (A) Fold increase over day 0 tumor volume following treatment. P, pIRES IL-12; V, control plasmid, pND2Lux; E, electroporation. Treatment mode of delivery: i.t., intratumor; i.m., intramuscular. A plus sign indicates treatment was administered; a minus sign indicates treatment was not administered. Initial treatment day is day 0; mice were treated again on day 7. Results for all groups (except P–E+ i.t. and V+E+ i.t.) represent the combined data from three replicate experiments, and error bars represent the standard error of the mean. The P–E+ i.t. and V+E+ i.t. treatment groups were tested in one experiment because existing data in our lab showed these treatments to be ineffectual. Error bars for these two groups represent standard deviation. The total number of samples for each treatment group are as follows: P–E–, n=16; P–E+ i.t. and V+E+ i.t., n=8; and for the remainder of groups, n=17. Mice were killed when tumor volume exceeded 1000 mm3. Data are expressed for surviving mice on each day.

In the following detailed description of the preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention.

Materials and Methods For IL-12

Tumor cells and mice. B16.F10 murine melanoma cells (CRL 6475; American Type Culture Collection, Rockville, Md.) were maintained in Dulbecco's minimal Eagle's medium (DMEM) supplemented with 10% FCS and 0.2% gentamicin. Cells were trypsinized and washed in sterile PBS before injection. The left flank of C57BL/6 mice (National Cancer Institute, Bethesda, Md.) was shaved and $1 \times 10^6$ cells in 50 µl of sterile PBS were injected subcutaneously. When challenged, mice were injected with $5 \times 10^5$ B16.F10 cells in the right flank. Tumors were measured using digital calipers, and treatment was begun when tumors reached 3-5 mm in diameter, ~7-10 days after injection. Tumor volume (v) was calculated using the formula $v = \alpha^2 b \pi / 6$, where $\alpha$=the smallest diameter and b=the perpendicular diameter. Mice were housed in accordance with AALAM guidelines.

Plasmid DNA. pIRES IL-12 was a gift from Karin Moelling (University of Zurich, Zurich, Switzerland). Briefly, pIRES IL-12 contains both subunits joined by an internal ribosomal entry site (IRES) behind a single cytomegalovirus (CMV) promoter. Robert Malone (Gene Delivery Alliance, Inc., Rockville, Md.) donated the pND2Lux, which encodes the reporter gene luciferase. Qiagen Mega Kits (Qiagen, Valencia, Calif.) were used for plasmid preparations. pIRES IL-12 was prepared with an endotoxin-free kit. All plasmid DNA was diluted in sterile injectable saline (0.9%) and stored at −20° C.

Intratumor treatment. Mice were anesthetized using 97% oxygen and 3% isoflurane. Tumors were injected with 50 µl (1 µg/ml) plasmid DNA in sterile saline using a tuberculin syringe with a 25-gauge needle. An applicator containing six penetrating electrodes ~1 cm in diameter was inserted into the tumor. Six pulses were delivered at 1500 V/cm (99 µs, 1 Hz) using a BTX T820 pulse generator (BTX, San Diego, Calif.).

Intramuscular treatment. Mice were anesthetized as described earlier. The skin surrounding the gastrocnemius muscle was shaved. Plasmid DNA diluted in sterile saline (50 µl, 1 µg/ml) was injected into the gastrocnemius muscle using a tuberculin syringe and a 25-gauge needle. An applicator specially designed for the mouse gastrocnemius containing four penetrating electrodes in a rectangular pattern was inserted into the muscle surrounding the injection site. A total of 12 pulses were delivered segmentally at 100 V/cm (20 ms, 1 Hz) using a BTX T820 pulse generator.

ELISA. Mice were humanely killed using CO2 asphyxiation, and then blood and tumors were collected on each day from four mice per treatment group. For detection of cytokines in the serum, blood was collected by cardiac puncture and stored at 4° C. overnight. Serum was extracted from blood samples by centrifugation (3 minutes at 5000 rpm) at 4° C., and stored at −20° C. until analyzed. To measure cytokine levels within the tumor tissue, the tumors were removed, frozen immediately on dry ice, weighed, and then stored at −80° C. For analysis, the tumors were thawed, and 1 ml of a solution containing PBS and 10% protease inhibitor cocktail (P8340; Sigma, St. Louis, Mo.) was added. The tissues were kept on ice, homogenized using a Power-Gen 700 (Fisher Scientific, Pittsburgh, Pa.), centrifuged for 3 minutes at 5000 rpm at 4° C., and then supernatants were assayed by ELISA. Both serum and tumor samples were analyzed using murine IFN-γ and IL-12 p70 ELISA kits (R&D Systems, Minneapolis, Minn.). Serum levels were calculated as pg of cytokine per ml of serum. Cytokine levels in the tumor were calculated as pg of cytokine per mg of tumor.

Histology. Mice were humanely killed by CO2 asphyxiation. Tumors were excised and placed in 50-ml conical tubes containing 10 ml of 10% formalin. The tissue was stained with H&E after fixation, as follows: after fixation in 10% neutral buffered formalin for 6 hours, representative tissue samples were processed into paraffin blocks using a Miles VIP tissue processor (Miles Inc., Mishawaka, Ind.). Briefly, tissues were dehydrated in ascending grades of ethanol, cleared in xylene, and infiltrated in paraffin (Tissue Prep 2; Fisher Scientific). Following embedding, tissues were sectioned on a standard rotatory microtome and 4-µm sections were retrieved from a water bath and mounted on glass slides. Three sections per tumor were examined. Sections were heat-dried and stained with H&E (Richard-Allan Scientific, Kalamazoo, Mich.) using standard histologic techniques. Using a synthetic mounting medium, coverslips were then placed.

Immunohistochemistry. Immunohistochemical staining was conducted to examine the tumors for the presence of CD4+ lymphocytes, CD8+ lymphocytes, and blood vessels using the following antibodies: rat anti-mouse CD4, rat anti-mouse CD8a (Ly2), and rat anti-mouse CD31 (PE-CAM-1), respectively (PharMingen, Cambridge, Mass.). Mice were humanely killed by CO2 asphyxiation. Tumors were excised with scissors and the skin removed, then immediately frozen in a mixture of dry ice and ethanol, and stored at (80° C. Frozen sections of 5 µm were obtained. For immunohistochemical analysis, rat antimouse CD4, rat anti-mouse CD8a (Ly2), or rat anti-mouse CD31 (PECAM-1) was applied to tissue sections at a dilution of 1.50 and incubated for 30 minutes, followed by detection with the Vector Elite Rat IgG-Peroxidase kit at 2× concentration (15 minutes each in biotinylated anti-rat IgG and ABC complex). Immunostaining was carried out on the Dako autostainer. Sections were analyzed at ×400 magnification.

Treatment of nude mice. BALB/c athymic nude mice were obtained from the National Cancer Institute and used at 7 weeks of age. B16.F10 cells were prepared as described earlier. Mice were injected subcutaneously in the left flank with $1 \times 10^6$ B16.F10 cells in 50 ml of sterile PBS. Treatment was begun when the tumors reached 3-5 mm in diameter. Mice received intratumor therapy as described earlier.

Statistical methods. Statistical analysis was performed by ANOVA or two-tailed Student's t-test.

FIGS. 1-7 provide the results of a two treatment protocol in accordance with the present invention. According to this protocol, IL-12 was delivered by in vivo electroporation. C57BL/6 mice were treated with established subcutaneous B16.F10 melanoma by injecting 50 µg (1 µg/ml) of plasmid DNA encoding IL-12 (pIRES IL-12) in sterile saline into the tumor or the gastrocnemius muscle, followed by electroporation. An applicator containing six penetrating electrodes was used to deliver 1500-V/cm, 100-µs pulses intratumorly. For intramuscular delivery, an applicator, specifically designed for the mouse gastrocnemius muscle and containing four penetrating electrodes, was used to administer 100-V/cm, 20-ms pulses, a protocol shown to result in high systemic IL-12 and IFN-γ expression. A single treatment did not result in long-term animal survival. Therefore, the following experiments administered a second treatment 7 days (day 7) after the initial treatment (day 0). Tumor size was evaluated throughout the experiment, and the results are presented as the fold increase over day 0 tumor volume for each treatment group as shown in FIG. 1A. Treatment with pIRES IL-12 injected intratumor, followed by electroporation slowed tumor growth, with nearly half, 8 out of 17, of the mice showing complete regression of their tumors. Progressive tumor growth was observed in mice receiving intramuscular injections of plasmid encoding IL-12 followed by electroporation. Mice not receiving electrical pulses, (P+E−), showed continued tumor growth until all mice were killed or succumbed to the tumor burden. Neither the administration of electroporation alone (P−E+) nor intratumor (i.t.) delivery of a control vector (pND2Lux) with electroporation (V+E+) decreased tumor growth. These results provide evidence that neither electrical pulses alone nor plasmid DNA is responsible for tumor regression. None of the treatment groups except the P+E+ i.t. group showed tumor regression, although P+E−i.t. did show slower tumor growth than P−E− through day 14 (P<0.05).

Figure 1B:
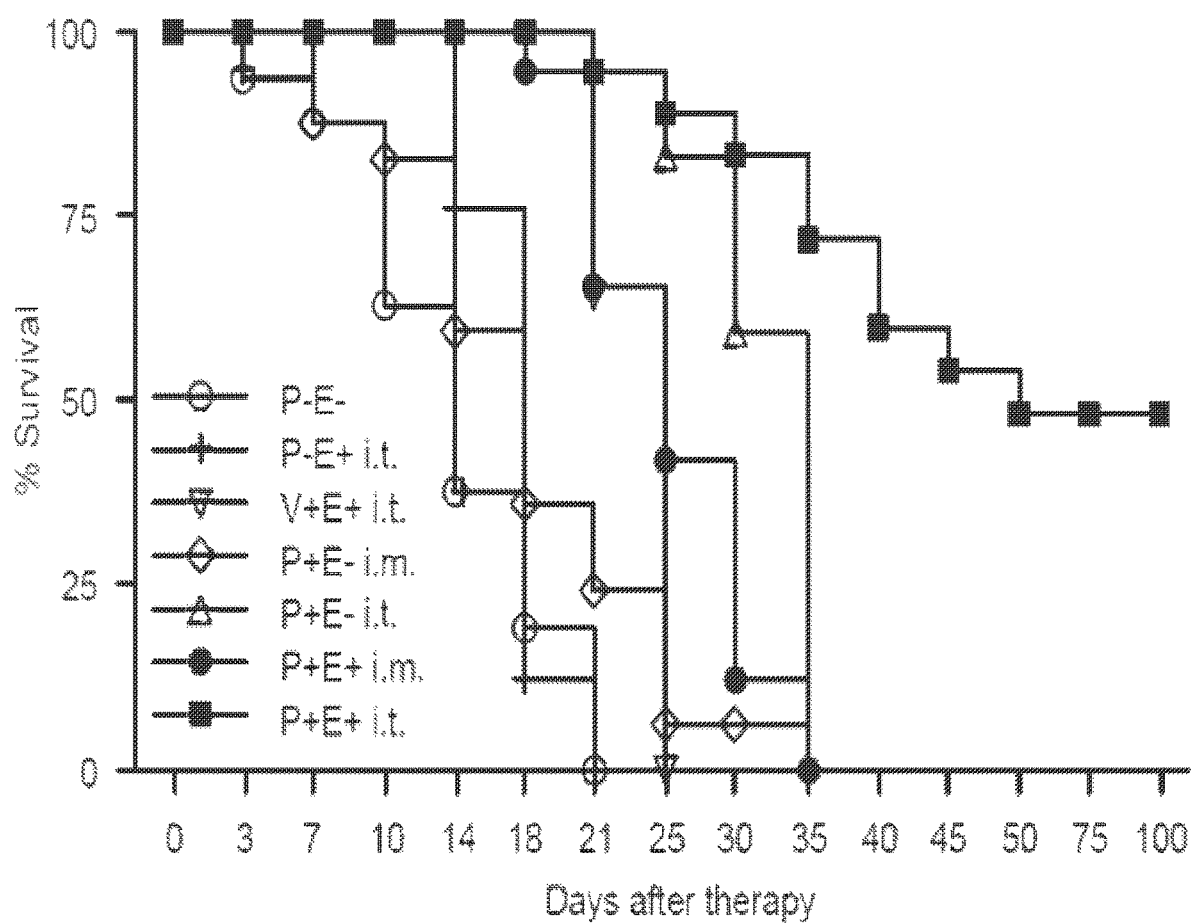
FIG. 1B is a graphical illustration of the administration of plasmid DNA encoding IL-12 followed by electroporation results in complete tumor regression.

Evaluation of mice 100 days after the initial treatment showed that 47% of mice, 8 out of 17, receiving intratumor delivery of IL-12 with electroporation were tumor-free as shown in FIG. 1B. These mice were considered cured. All mice receiving i.t. treatment with IL-12 and electroporation experienced prolonged survival compared with animals in other treatment groups. None of the mice in the control groups survived longer than 35 days. Specifically, if left untreated or treated with pulses alone, mice did not survive longer than 21 days.

We challenged seven of the animals that showed complete regression and remained disease-free for 50 days in the right flank with B16.F10 tumor cells. No additional treatments were administered. Of the seven challenged, five were resistant to tumor growth on the right flank, while tumors grew in 100% of naive mice. This result suggests the development of an immune memory response following treatment of the initial subcutaneous tumor established on the left flank.

Figure 2A:
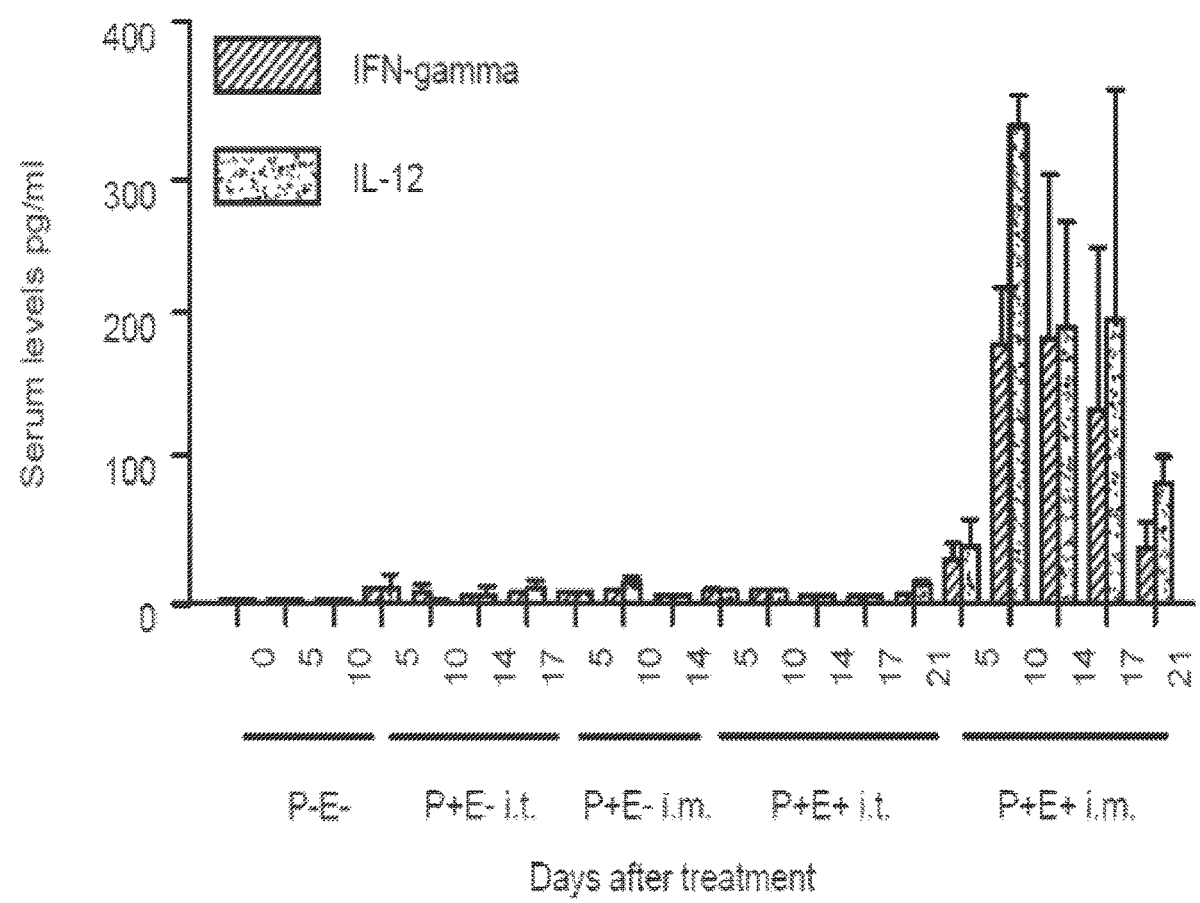
FIG. 2A is a graphical illustration of the results of the analysis of serum and tumor tissue for IL-12 and IFN-γ expression. P, pIRES IL-12; E, electroporation. Mode of delivery: i.t., intratumor; i.m., intramuscular. Serum levels of IL-12 and IFN-_ in tumor-bearing mice. For each treatment group on each day tested, n=4 mice. Error bars represent standard deviation.

As mentioned earlier, IL-12 induces several effects on the immune system. To evaluate the cytokine expression induced by either intramuscular or intratumor treatment, serum was analyzed and tumor levels of IL-12 and IFN-γ. Serum levels of both cytokines were highest after intramuscular injection followed by electroporation as illustrated by FIG. 2A. Serum IL-12 peaked at 320 pg/ml 10 days after treatment, whereas serum IFN-γ induced by IL-12 expression peaked at 177 pg/ml on day 14. Serum levels of both cytokines were significantly greater from mice treated intramuscularly with electroporation than other treatments on days 5, 10, and 14 (P<0.05). Serum levels of these cytokines in mice treated with intratumor injection followed by electroporation were not significantly greater than expression in mice that received no treatment (P>0.05).

Figure 2B:
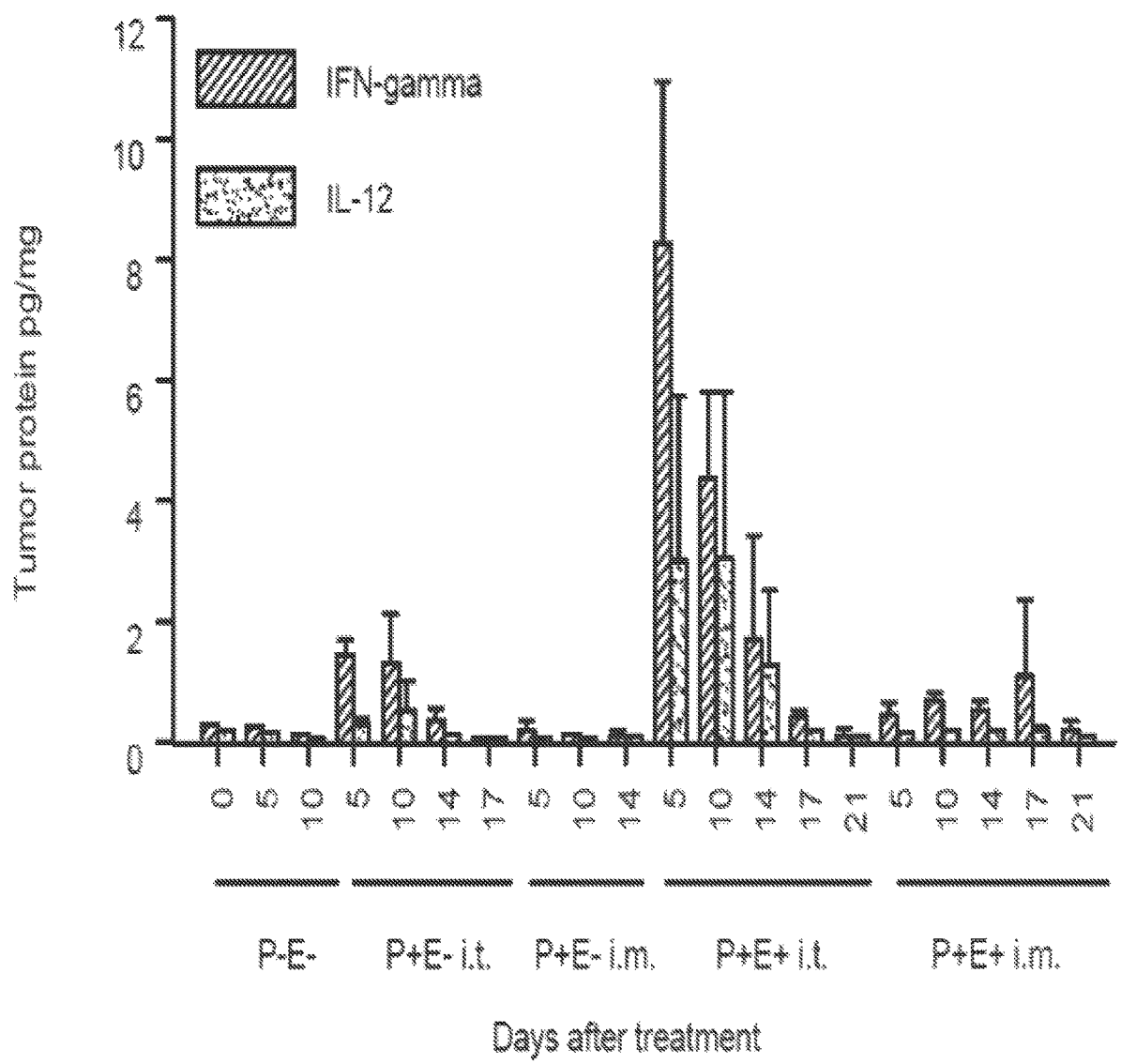
FIG. 2B is a graphical illustration of the results of the analysis of serum and tumor tissue for IL-12 and IFN-γ expression. P, pIRES IL-12; E, electroporation. Mode of delivery: i.t., intratumor; i.m., intramuscular. Mean tumor expression of IL-12 and IFN-_. For each treatment group on each day tested, n=4 mice. Error bars represent standard deviation.

Analysis IL-12 and IFN-γ expression within the tumors revealed that intratumor treatment with electroporation resulted in the presence of these cytokines at the tumor site (FIG. 2B). Intratumoral IL-12 reached 3 pg/mg of tumor tissue on day 5 and remained at that level through day 10, whereas IFN-γ levels peaked at 8.16 pg/mg of tumor on day 5. Treatment with ORES IL-12 injected intratumorly followed by electroporation produced significantly higher (P<0.05) IFN-γ levels than other treatment groups on days 5 and 10. Although tumor expression of IL-12 reached 3 pg/mg of tumor with intratumor treatment, as opposed to 0.64 pg/mg of tumor with intramuscular treatment, these levels were not significantly greater (P>0.05) as a result of a wide spectrum of expression levels in these tumors after intratumor treatment (0.5-6.9 pg/mg of tumor tissue).

Treatment with intramuscular injection followed by electroporation did not result in significant (P>0.05) cytokine expression within the tumors as shown in FIG. 2B. Following intramuscular treatment the highest IFN-γ expression measured was 1 pg/mg of tumor on day 17. Therefore, treatment protocols that did not result in tumor regression also did not produce intratumoral IL-12 or IFN-γ expression. These results support previous reports on the critical need for cytokine expression within the tumor.

Figure 3A:
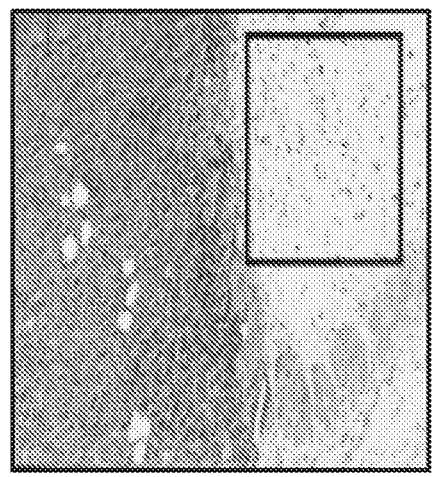
FIG. 3A-C is an illustration of representative sections of tumor tissue, 5 days after treatment, analyzed by H&E staining for infiltrating immune cells. Three sections per tumor were examined. All sections are shown at ×250 magnification. An area containing immune cells is marked by a box. (A) No treatment. (B) Administration of IL-12 i.m. with electroporation. (C) Administration of IL-12 i.t. with electroporation.
Figure 3B:
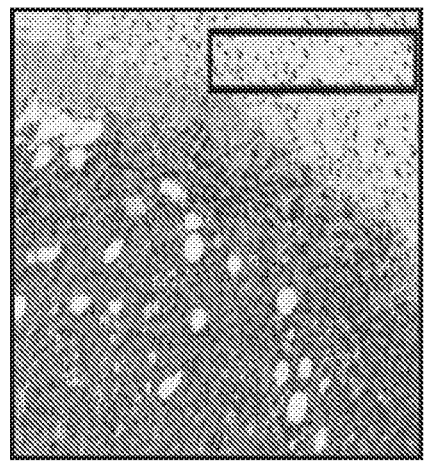
Figure 3C:
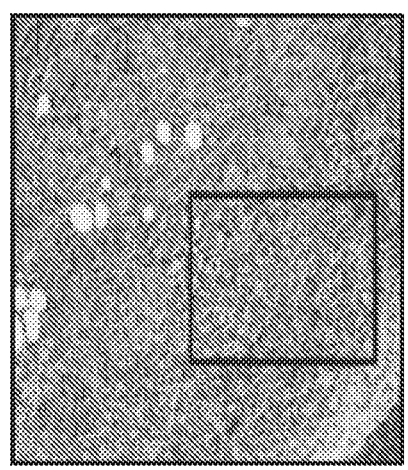

Resistance to challenge following successful tumor regression suggests the development of an immune memory response. The tumors were examined histologically 5 days after initial treatment to evaluate the influx of immune cells to the tumor. Tumor sections were stained with hematoxylin and eosin (H&E) to distinguish infiltrating immune cells from tumor cells. The H&E-stained sections showed infiltration of lymphocytes into the tumors of mice 5 days after receiving intratumor injection of pIRES IL-12 followed by electroporation as shown in FIG. 3C. In contrast, mice not treated or receiving intramuscular treatment with electroporation did not display a great influx of lymphocytes as illustrated in FIGS. 3A and 3B. Treatment protocols not including in vivo electroporation (P+E− either intratumor or intramuscular) also did not result in the influx of lymphocytes (data not shown).

Figure 4A:
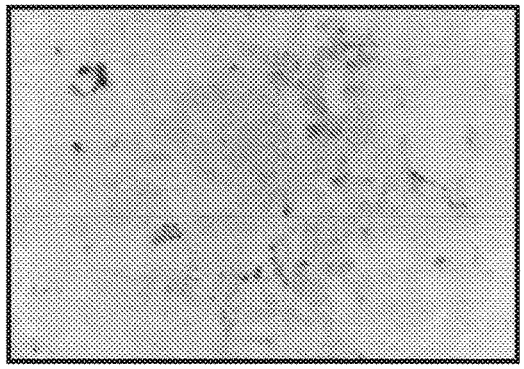
FIG. 4A-F is an illustration of representative sections of tumor tissue, 5 days after treatment, analyzed by immunohistochemistry for the stained brown. An arrow in (B) points to a cell representative of positive staining. (A, B) Staining for CD4+ lymphocytes and CD8+ lymphocytes, respectively, from untreated tumors. (C, D) Staining for CD4+ lymphocytes and CD8+ lymphocytes, respectively, from tumors receiving i.t. injection of plasmid DNA encoding IL-12 followed by electroporation. (E, F) Staining for CD4+ lymphocytes and CD8+ lymphocytes, respectively, from tumors following i.m. administration of plasmid DNA encoding IL-12 with electroporation.
Figure 4B:
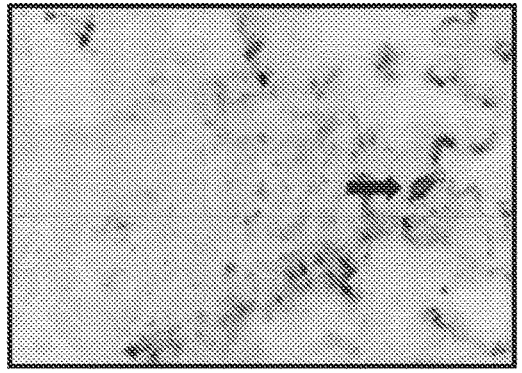
Figure 4C:
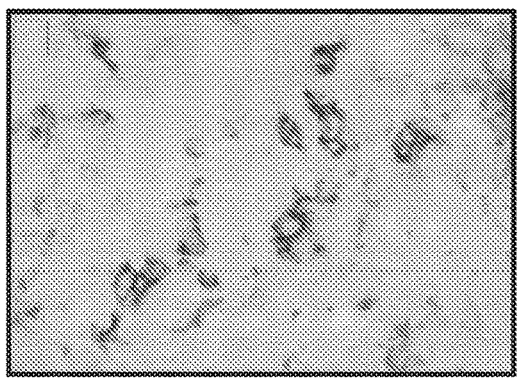
Figure 4D:
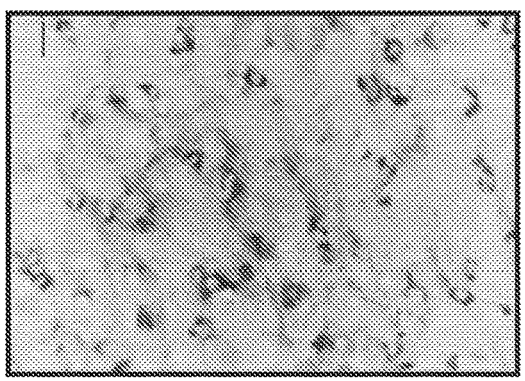
Figure 4E:
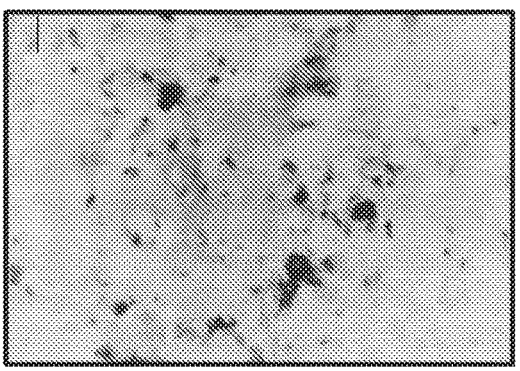
Figure 4F:
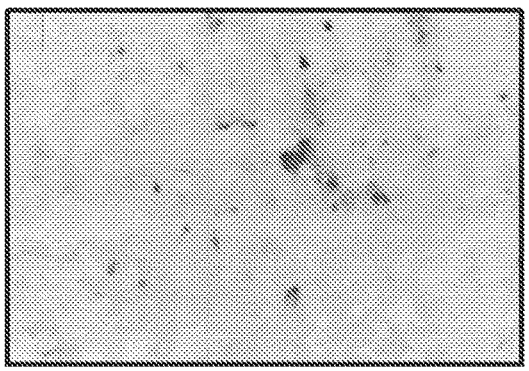

By immunohistochemical phenotyping, it is demonstrated that the lymphocytes observed in tumors following intratumor treatment with IL-12 and electroporation were CD4+ and CD8+ T cells as illustrated in FIGS. 4C and 4D. In comparison, lymphocytes were observed in limited numbers in untreated tumors as shown in FIGS. 4A and 4B. Treatment of mice with intramuscular injection followed by electroporation also resulted in limited lymphocytic infiltrate, similar to that characterizing the untreated control group of FIGS. 4E and 4F. Additionally, mice receiving injection of plasmid encoding IL-12 (P+E− intratumor or intramuscular) or control plasmid with electroporation (V+E+ intratumor) did not show infiltrating lymphocytes (data not shown).

Figure 5A:
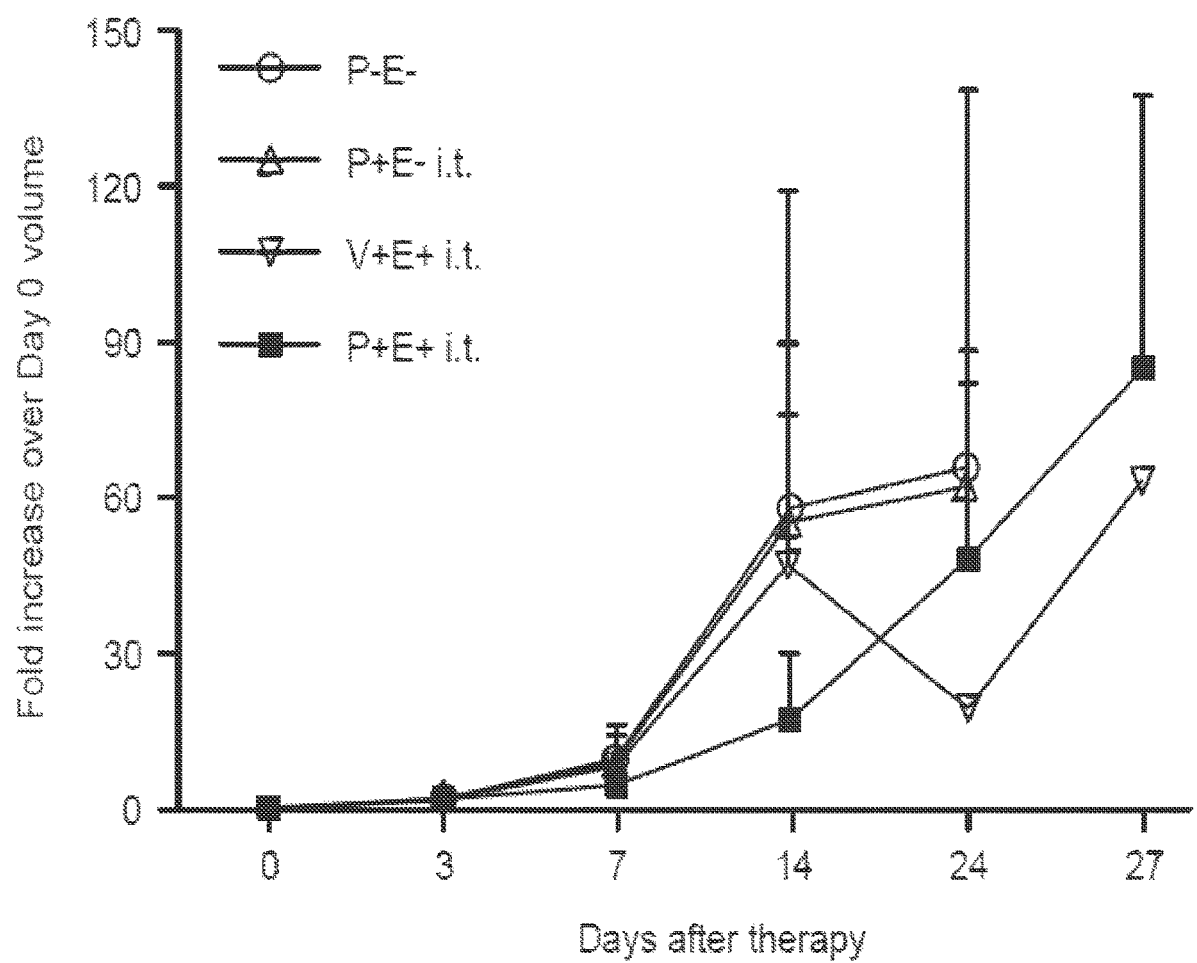
FIG. 5A is a graphical illustration of the administration of IL-12 followed by electroporation which does not result in tumor regression in a nude mouse model. Fold increase over day 0 tumor volume following treatment. P, pIRES IL-12; V, control plasmid, pND2Lux; E, electroporation. Mode of delivery: i.t., intratumor. Initial treatment day is day 0; mice were treated again on day 7. The data represent two experiments each, with four mice in each group. Error bars represent standard deviation. Mice were killed when tumor volume exceeded 1000 mm3. Data are expressed for surviving mice on each day.
Figure 5B:
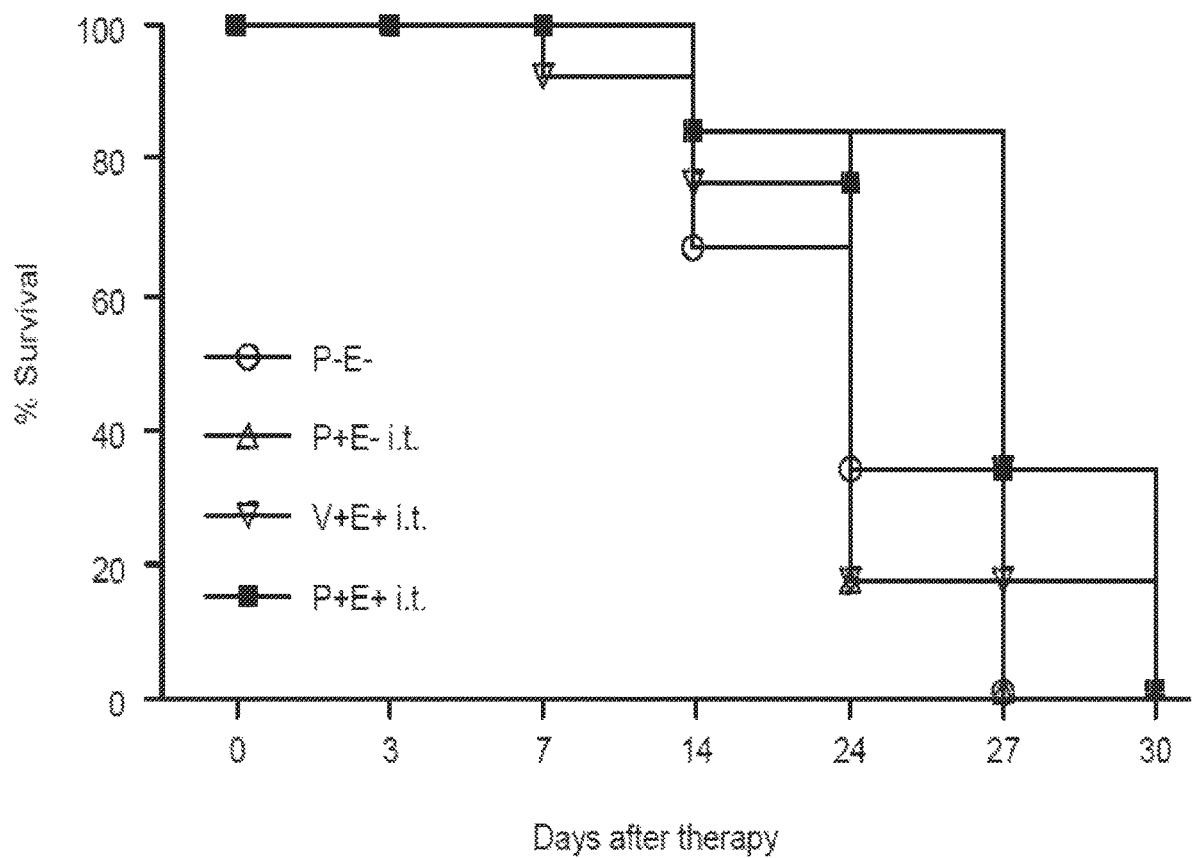
FIG. 5B is a graphical illustration of the administration of IL-12 followed by electroporation which does not result in tumor regression in a nude mouse model.

To further evaluate the need for T lymphocytes in tumor regression, athymic nude mice deficient in T cells were used as the mouse model in place of C57BL/6 mice. These mice were injected with B16.F10 tumor cells subcutaneously and began treatment when tumors reached 3-5 mm in diameter. Mice received intratumor treatments as explained earlier: intratumor injections of plasmid encoding IL-12 without electroporation, intratumor injection of a control plasmid followed by electroporation, or intratumor injections of plasmid encoding IL-12 followed by electroporation. Because of the lack of successful response in C57BL/6 mice following intramuscular injection, we administered only intratumor treatments. None of the treatments in the nude mouse model resulted in tumor regression as shown in FIG. 5A. In addition, no mice in any treatment group survived longer than 30 days. This observation further suggests the necessity of a T-cell response for successful regression of B16.F10 melanoma tumors.

Figure 6A:
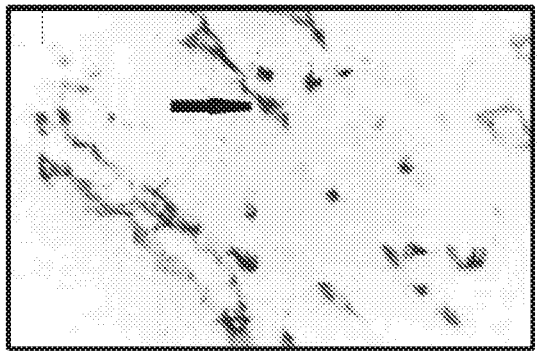
FIG. 6A-D is an illustration of the immunohistochemical analysis of tumor tissue for the presence of blood vessels. Representative sections rich in vessels are depicted for each treatment. Three sections per tumor were examined. All sections are shown at _400 magnification. An arrow in (A) points to a representative blood vessel. (A) Presence of blood vessels within tumors on day 0, before treatment. (B) Untreated tumors on day 5. (C) Tumors on day 5 from mice receiving i.m. injection of plasmid DNA encoding IL-12 followed by electroporation. (D) Blood vessels on day 5 from mice receiving i.t. administration of plasmid DNA encoding IL-12 followed by electroporation.
Figure 6B:
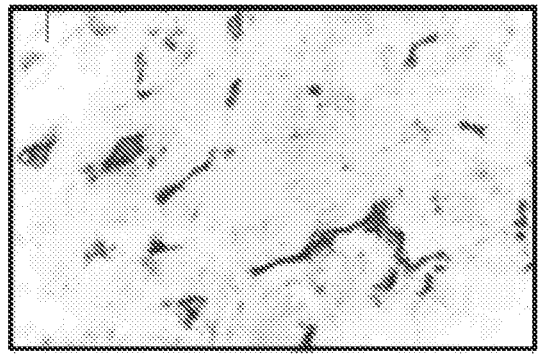
Figure 6C:
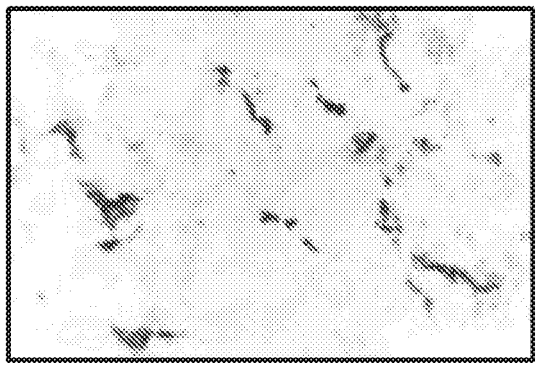
Figure 6D:

Another potential role of IL-12 on tumor regression is its effect on angiogenesis. To assess the antiangiogenic role of IL-12 on B16.F10 tumors in C57BL/6 mice, representative sections of three tumors from each treatment group were stained with anti-CD31 antibodies, marking endothelial cells. Five different areas of highest vascularity were examined at a magnification of ×400 for each group as illustrated by FIG. 6. A representative section of the vessels in an untreated tumor on day 0 is shown in FIG. 6A. FIGS. 6B and 6C show the large number of vessels present within untreated tumors or tumors from mice receiving intramuscular injection followed by electroporation on day 5. In contrast, FIG. 6D shows the reduction of blood vessels after intratumor injection and electroporation on day 5. Tumors from mice receiving injection of plasmid encoding IL-12 without electroporation (P+E− intratumor or intramuscular) or control plasmid with electroporation (V+E+) did not show a reduction in vasculature (data not shown).

In addition, vessels in each of the three tumors excised from untreated mice were counted, mice receiving intramuscular IL-12 and electroporation, and mice receiving intratumor IL-12 and electroporation. In FIG. 7, Table 1 shows the number of blood vessels counted in the field of highest vascularity at a magnification of ×400 for each of the three excised tumors. Only intratumor injection followed by electroporation (P+E+ intratumor) resulted in significant (P<0.05) vessel reduction compared with untreated animals. Although an antiangiogenic effect was observed following intratumor treatment with electroporation, the lack of response in the nude mouse model suggests that T cells may be a critical factor for obtaining regression of B16.F10 melanoma. An antiangiogenic response may, however, contribute to stabilization of tumor size while an immune response is mounted.

This report has demonstrated that IL-12 delivered in the form of plasmid DNA with the aid of electroporation can result in successful regression of B16.F10 tumors. The animals remain disease-free and are resistant to challenge at a distant site. The results of the two treatment protocol demonstrate nearly a 47% survival rate following gene therapy treatment of established subcutaneous B16.F10 melanoma.

In summary, the present invention provides a treatment modality that can eradicate established B16.F10 melanoma tumors and result in resistance to renewed tumor growth following challenge. Utilizing the two treatment protocol, after i.t. delivery of plasmid DNA encoding IL-12 by in vivo electroporation, 47% of mice showed complete regression of their tumors and remained disease-free. These mice were challenged with B16.F10 tumor cells, and five of seven remained tumor-free for an additional 100 days, after which they were humanely killed. Also, it is demonstrated that i.t. injection of plasmid DNA encoding IL-12 and electroporation is more effective than i.m. delivery for promoting tumor regression and prolonging animal survival. The success of this treatment in this tumor model stems from the local expression of IL-12 and IFN-γ, infiltrating lymphocytes, and inhibition of angiogenesis within the treated tumor.

FIGS. 8-12 are illustrative of the three-treatment protocol in accordance with the present invention. Regarding the short-term prevention of subcutaneous tumors at a distant site, C57B1/6 mice were shaved on both flanks. Mice were injected subcutaneously in the left flank with $1\times10^6$ B16.F10 cells in 50 μl of sterile PBS. Once tumors were established, measuring 3-5 mm in diameter, treatment was begin. Two types of experiments were performed. The first series of experiments, on the day of the first treatment, $5\times10^5$ B16.F10 cells in 50 μl of sterile PBS were injected in the right flank of mice. The second set of experiments, $5\times10^5$ B16.F10 cells in 50 μl of sterile PBS were injected in the right flank of mice three days after the left flank injection. For both sets of experiments, mice received intratumor or a combination of intratumor and intramuscular therapy to the initial tumor on the left flank as described previously. Pulse protocols are further described within the results section. Established tumors on the left flank were continuously measured as described earlier, and the right flanks of the mice were monitored for tumor development.

Regarding the analysis of lung colonization, B16.F10 cells were prepared as previously detailed for subcutaneous injection. Either $1\times10^5$ or $5\times10^5$ B16.F10 cells in 50 μl of sterile PBS were injected into the tail vein using a 1 cc syringe with a 30-gauge needle. Mice received intra-muscular treatment on the day of inoculation and four days later as described earlier. Twenty-one days following inoculation, mice were euthanized and their chest cavities exposed. Lung colonies appeared as black tumor nodules on the lung surface and were counted.

As shown previously with the two-treatment protocol, a 47% disease-free survival rate for greater than 100 days in mice bearing established subcutaneous B16.F10 tumors treated twice with i.t. injection of plasmid encoding IL-12 and electroporation. Five out of seven disease free mice were resistant to challenge following an additional inoculation of tumor cells in the opposite flank. We previously noted a poor response to the first treatment was often observed in tumors that did not fully regress. By the second treatment seven days later, these tumors had shown extensive growth and could possibly have been too large for successful regression by the additional treatment. Increases in the disease free survival rate were obtained by two methods. First, instead of two treatments three treatments were delivered to these mice on days 0, 4, and 7. Second, an intramuscular treatment was added. As discussed earlier, it has been shown that intra-muscular delivery of IL-12 plasmid results in a systemic production of IL-12 and IFN-γ (41). These mice also received three treatments.

Figure 8A:
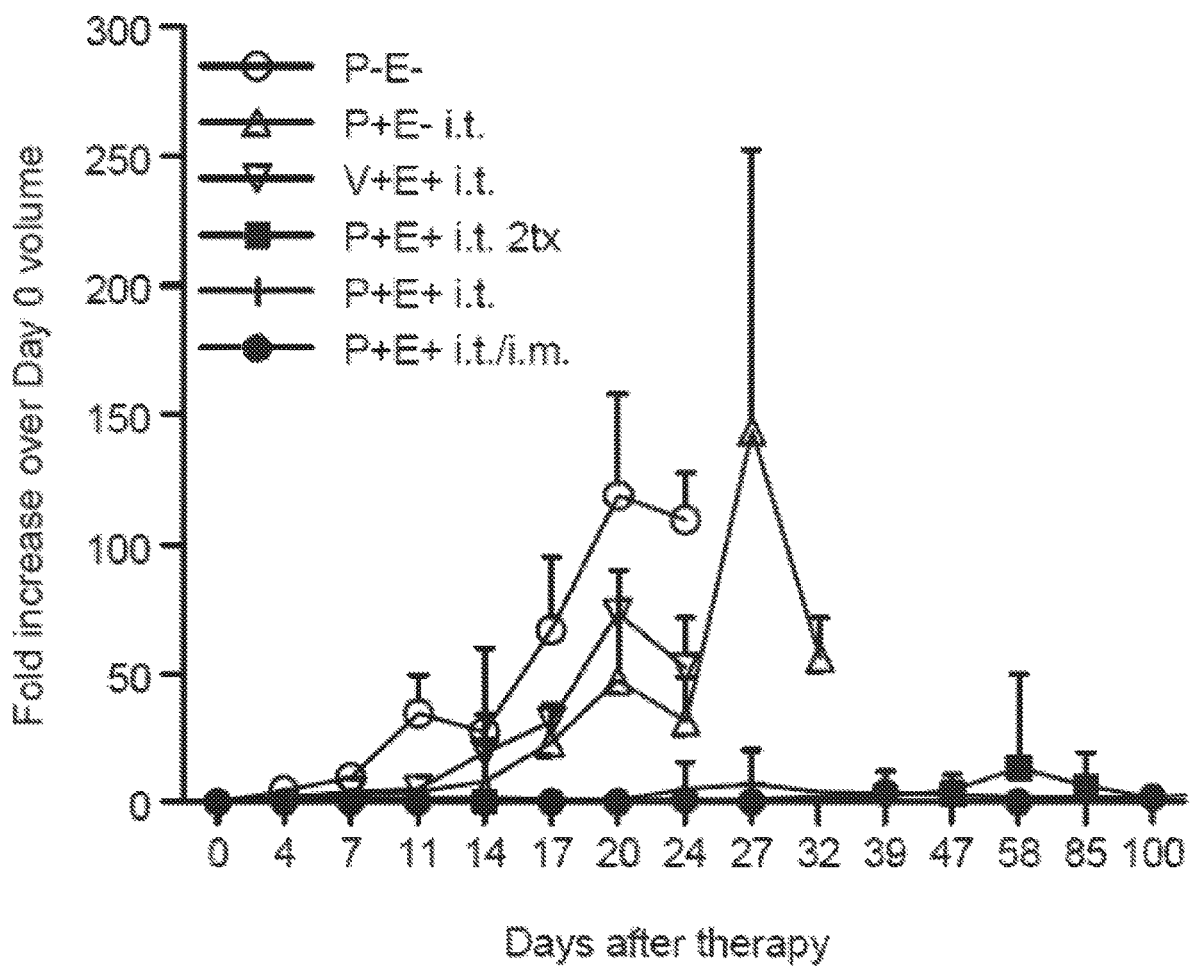
FIG. 8A is a graphical illustration of the three treatment protocol in accordance with the present invention. For the three treatment protocol, day 0 is the day of the initial treatment and mice were treated again on days 4 and 7. (A) Fold increase of tumor volume compared to tumor volume on day of first treatment. Data is expressed for surviving mice on each day. P=pIRES IL-12; V=control plasmid, pND2Lux; E=electroporation. For location of treatment, i.t.=intratumor delivery; i.m.=intramuscular delivery.
Figure 8B:
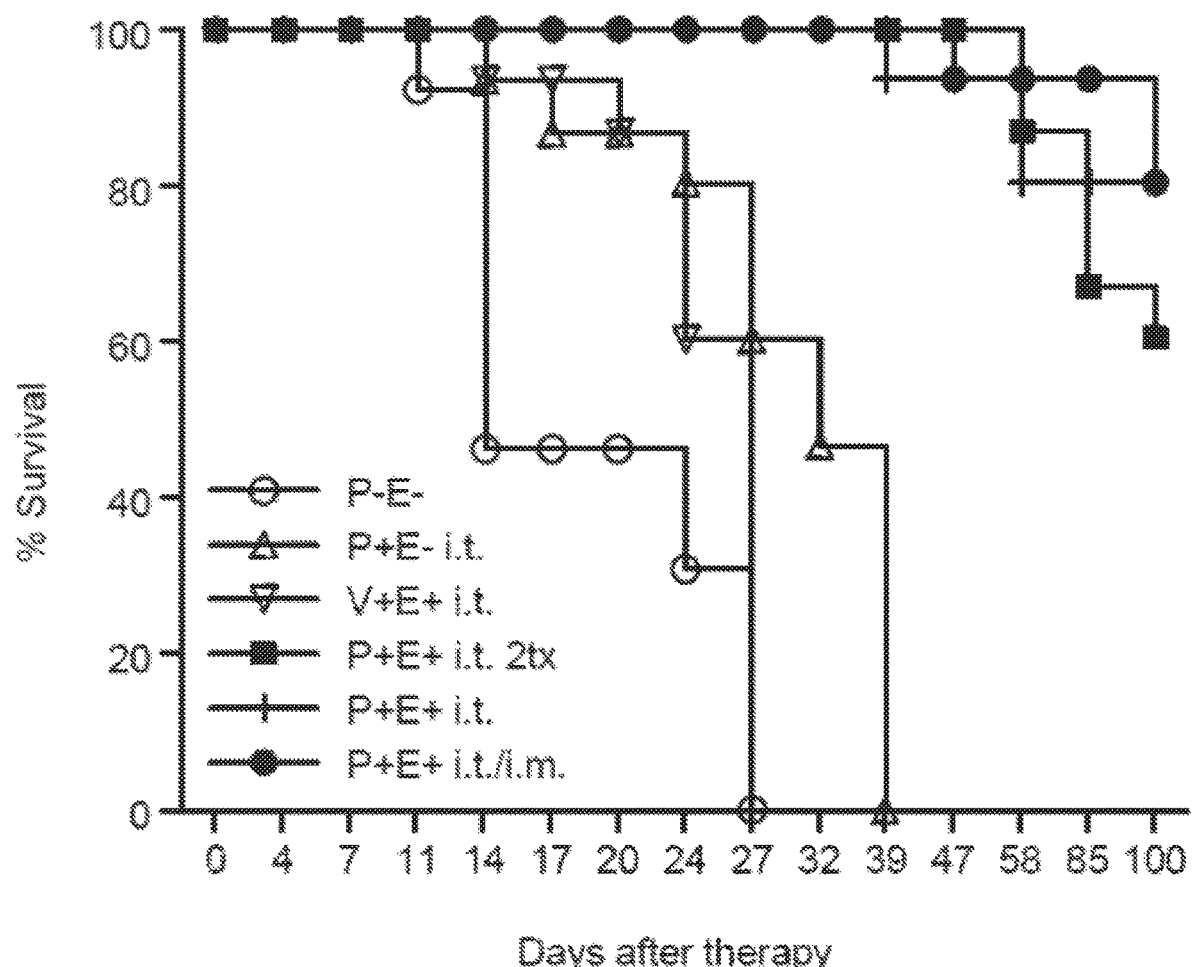
FIG. 8B is a graphical illustration of the three treatment protocol in accordance with the present invention. For the three treatment protocol, day 0 is the day of the initial treatment and mice were treated again on days 4 and 7.

The administration of three-treatments, whether i.t. alone or in combination with i.m., resulted in complete tumor regression and an increased disease free survival rate over two treatments as illustrated by FIG. 8. Both three-treatment protocols (i.t. alone or i.t. and i.m.) resulted in an 80% disease free survival rate, statistically significant (p<0.05) over the 60% disease free survival rate resulting from the two-treatment protocol (FIG. 1b). The slight increase in the disease free survival rate with the two-treatment protocol over our previous results with two treatments (60% vs. 47%) was not statistically significant. All three of the treatment protocols delivering IL-12 plasmid by electroporation resulted in complete regression of the tumors and maintenance of a disease free status through 100 days. When challenged with B16.F10 cells, all 12 (100%) of the disease free mice in the three treatment groups were resistant, and eight out of nine mice (88.9%) in the two-treatment group were resistant, suggesting the development of an immune memory response. These treatment protocols were further examined in multiple tumor and metastatic models.

The experiments described above demonstrated that the formation of new tumors (opposite flank) could be prevented in a high percentage of mice that had a complete response and long-term disease free survival. To further examine the potential of this therapeutic approach, it was important to evaluate the ability to block the formation of new tumors prior to the regression of the primary tumor. On the same day that mice received the first treatment for an established B16.F10 tumor on the left flank, a second injection of B16.F10 cells were administered to the right flank. Mice were then evaluated for regression of the first tumor as well as prevention of establishment of the second tumor.

Figure 9A:
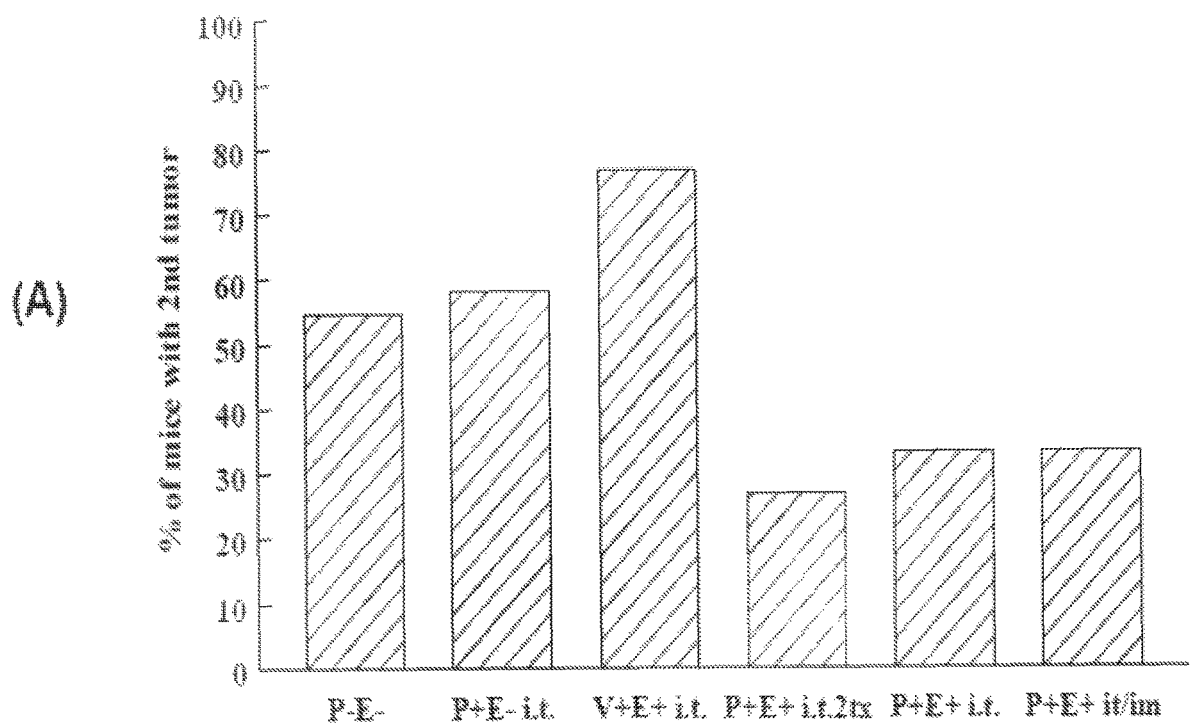
FIG. 9A is a graphical illustration of the short-term prevention of second tumors in accordance with the present invention. Three treatments were administered on days 0, 4, and 7 and two treatments administered on days 0 and 7. Percent of mice that had a tumor form on the right flank, which received no treatment. Data represents three replicate experiments with an n of 5 each. P=pIRES IL-12; V=control plasmid, pND2Lux, E=electroporation. For location of treatment, i.t.=intratumor delivery; i.m.=intramuscular delivery.
Figure 9B:
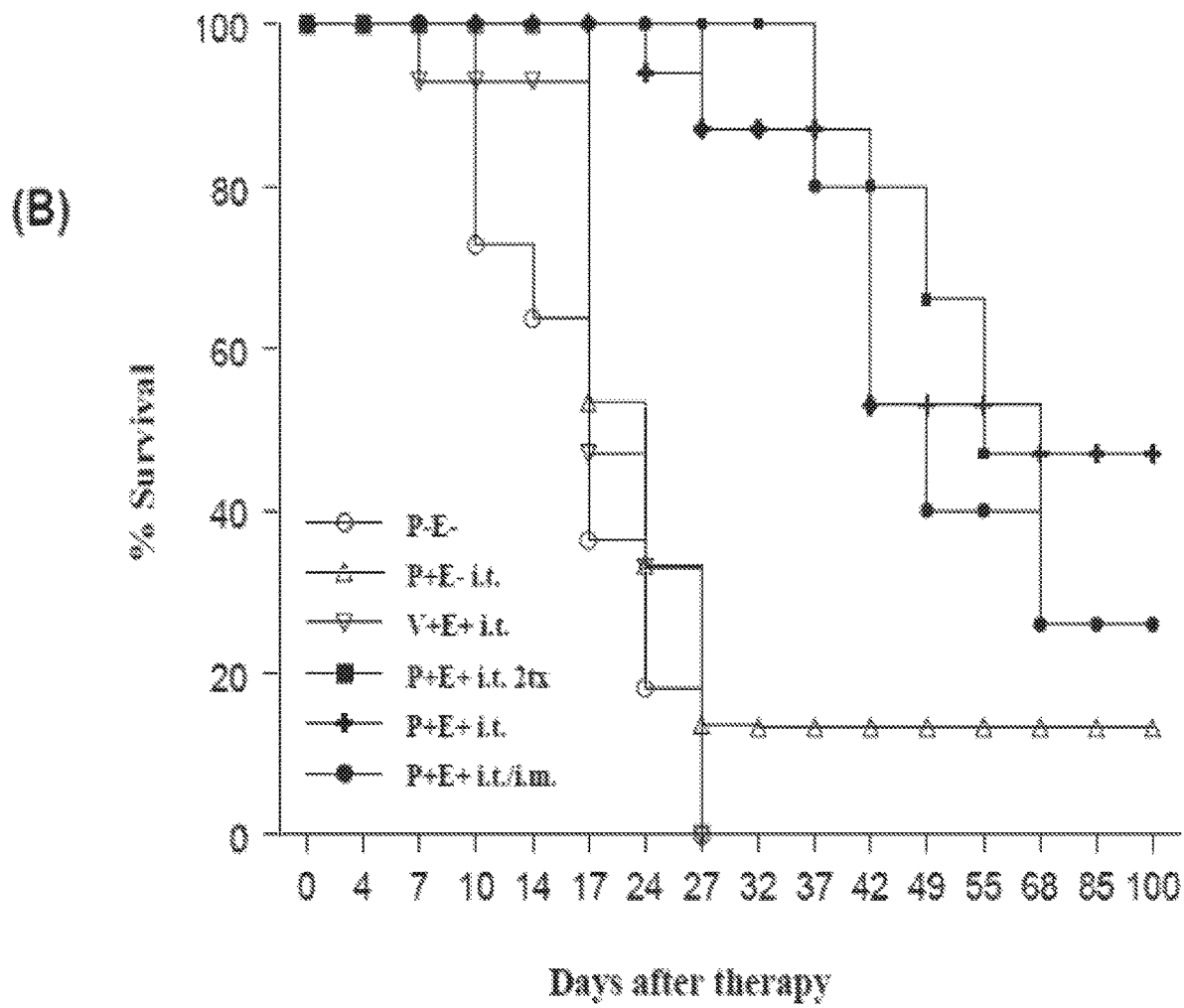
FIG. 9B is a graphical illustration of the short-term prevention of second tumors in accordance with the present invention. Three treatments were administered on days 0, 4, and 7 and two treatments administered on days 0 and 7. Percent survival of mice following treatment; 5×10$^5$ B16.F10 cells were injected on the right flank on day 0, at a time that the established tumor on the left flank was treated. Mice were euthanized when tumor volume exceeded 1000 mm$^3$. Data represents three replicate experiments with an n of 5 each. P=pIRES IL-12; V=control plasmid, pND2Lux; E=electroporation. For location of treatment, i.t.=intratumor delivery; i.m.=intramuscular delivery.

Treatment protocols that involved i.t. or i.t./i.m. injections and electroporation resulted in regression of the primary tumors as well as prevention of the establishment of the secondary tumor (FIG. 9a, b). Secondary tumors developed in 27% mice receiving two treatments and 33% mice receiving either of the three treatment protocols (FIG. 9a). Of the mice receiving an i.t. injection of control plasmid followed by electroporation, 77% of mice developed secondary tumors. In the no treatment group, 55% mice developed the secondary tumor and 58% mice grew the second tumor in the group receiving i.t. injection only (FIG. 9a). Because of the aggressiveness of this tumor model, several mice in the control treatment groups succumbed to their primary tumor before the secondary tumor could develop. Therefore, the percentage of mice developing the secondary tumor may have been higher in these groups had the mice survived for a longer period of time. Survival (FIG. 9b) was significantly improved (p<0.01) in all three groups that received both IL-12 plasmid and electroporation compared to no treatment, plasmid injection alone and injection of control plasmid followed by electroporation. The mean survival for each group was as follows: no treatment=17.9+/−6.7 days; plasmid injection alone=30.1+/−28.9 days; control plasmid followed by electroporation=20.6+/−6.0 days; i.t. and i.m. plasmid injection and electroporation (3 treatments)=59.5+/−27.7 days; i.t. plasmid injection and electroporation (2 treatments)=65.2+/−24.0 days; i.t. plasmid injection and electroporation (3 treatments)=68.6+/−31.8 days. Seven out of 15 (47%) mice treated with i.t. plasmid injection and electroporation (3 treatments) were considered "cured" as they had no evidence of disease 100 days post treatment. In the i.t./i.m. three treatment and the i.t. two treatment group 4 out of 15 (26%) were "cured".

Figure 10A:
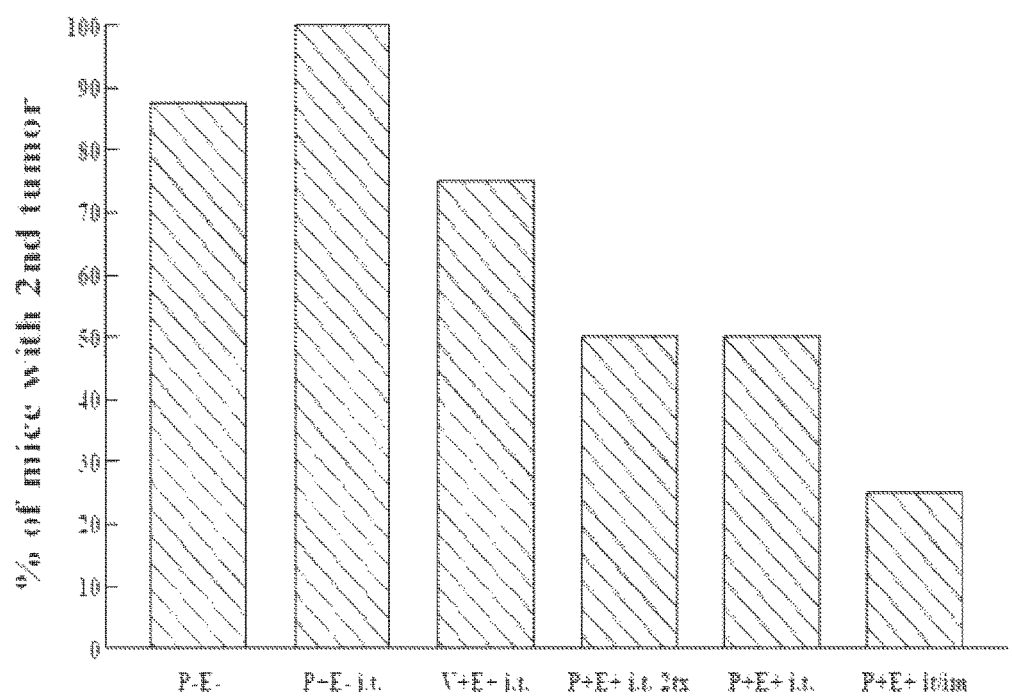
FIG. 10A is a graphical illustration of the prevention of second tumor induced prior to initiation of therapy. Three treatments were administered on days 0, 4, and 7 and two treatments administered on days 0 and 7. Percent of mice that had a tumor form on the right flank, which received no treatment. Mice were euthanized when tumor volume exceeded 1000 mm$^3$. Data represents three replicate experiments with an n of 5 each. P=pIRES IL-12; V=control plasmid, pND2Lux; E=electroporation. For location of treatment, i.t.=intratumor delivery; i.m.=intramuscular delivery.
Figure 10B:
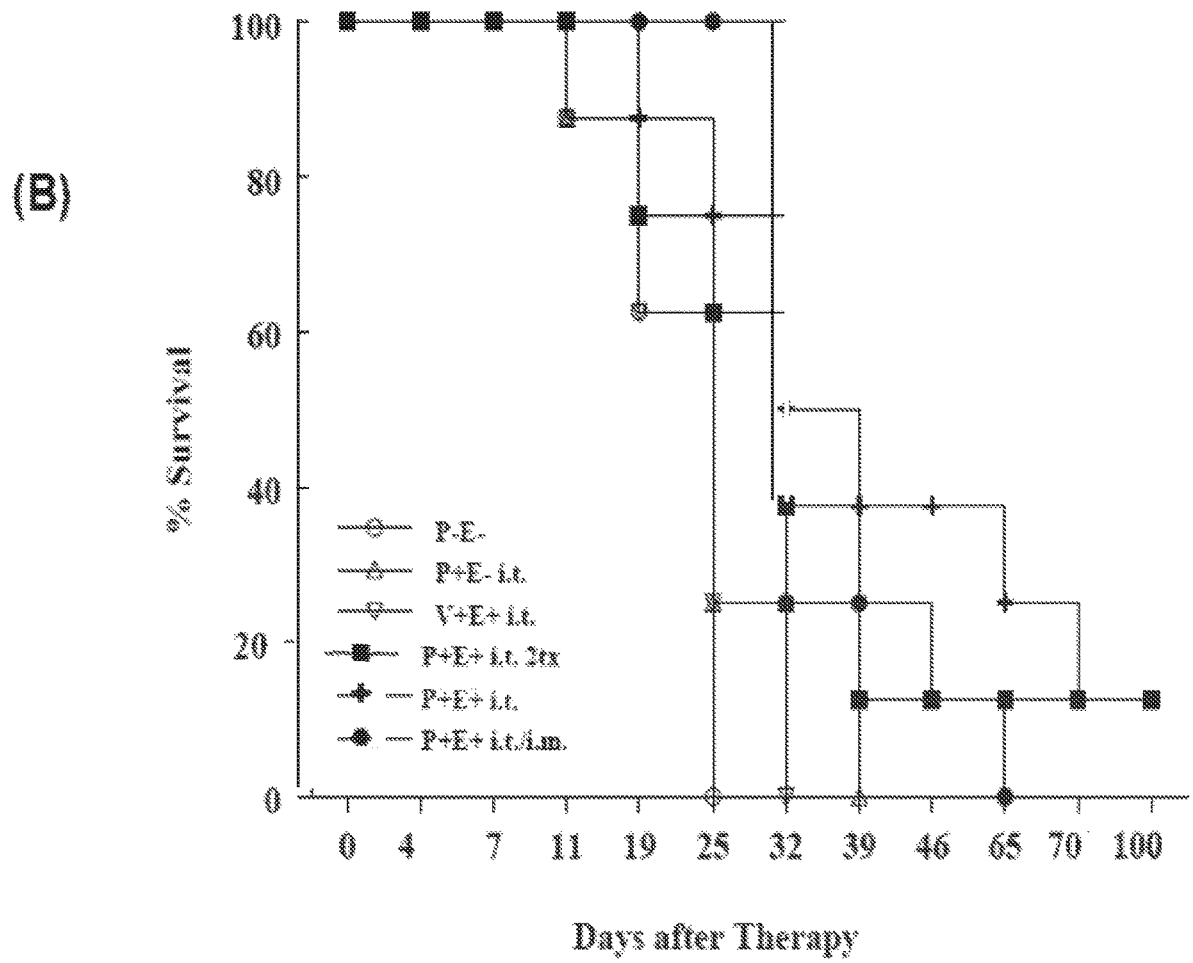
FIG. 10B is a graphical illustration of the prevention of second tumor induced prior to initiation of therapy. Three treatments were administered on days 0, 4, and 7 and two treatments administered on days 0 and 7. Percent survival of mice following treatment; 5×10$^5$ B16.F10 cells were injected on the right flank. Three days after cells were injected on the left flank. Mice were euthanized when tumor volume exceeded 1000 mm$^3$. Data represents three replicate experiments with an n of 5 each. P=pIRES IL-12; V=control plasmid, pND2Lux; E=electroporation. For location of treatment, i.t.=intratumor delivery; i.m.=intramuscular delivery.
Figure 12:
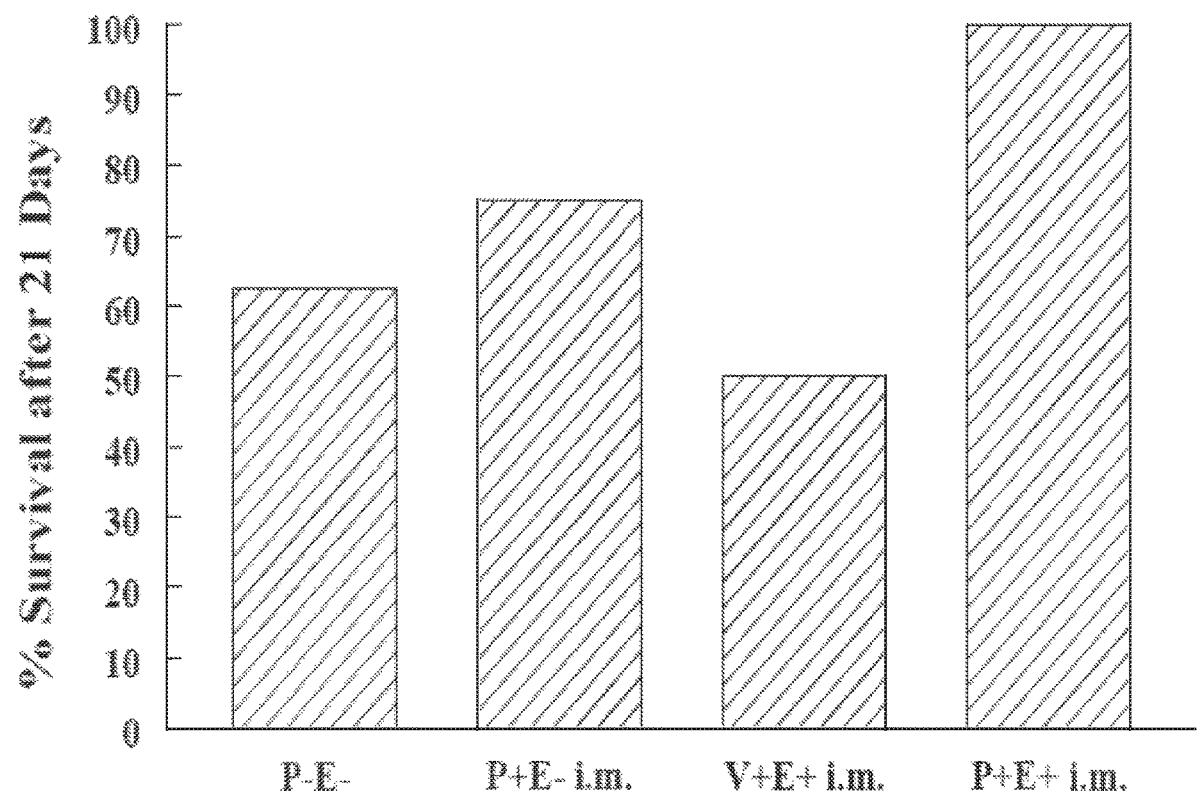
FIG. 12 is a graphical illustration of the survival rate of mice receiving a high dose of B16 cells intravenously. Three treatments were administered on days 0, 4, and 7. Mice were followed for 21 days and then euthanized. Data represents two replicate experiments with an n of 4 in each. Mice received an injection of 5×10$^5$ B16.F10 cells to the tail vein on day 0, at the time of treatment by delivering plasmid intramuscularly. P=pIRES IL-12; V=control plasmid, pND2Lux; E=electroporation.

A second series of experiments was performed to examine if this approach could prevent formation of distant subcutaneous tumors when the tumor cells were injected prior to treatment. Three days after mice received an injection of B16 cells in the left flank (approximately four days before mice received treatment for the established B16.F10 tumor on the left flank) we administered a second injection of B16.F10 cells to the right flank. As in the previous experiment, mice were evaluated for regression of the first tumor as well as prevention of establishment of the second tumor (FIG. 10a, b). Secondary tumors developed in 50% of mice receiving two or three i.t. treatments and 25% of mice receiving three i.t. and i.m. treatments (FIG. 10a). In the control groups: 100% of mice receiving i.t. injection of IL-12 plasmid without electroporation, 87.5% of the no treatment group and 75% of the mice receiving an i.t. injection of control plasmid followed by electroporation developed secondary tumors (FIG. 10a). A significant increase (p<0.05) in survival was seen only in mice receiving three i.t. or i.t./i.m. treatments (FIG. 10b) compared to the 3 control groups. Survival of mice in the i.t. two treatment group was not significantly different than any of the other groups. The mean survival for each group was as follows: no treatment=21.8+/−4.8 days; plasmid injection alone=26.0+/−8.8 days; control plasmid followed by electroporation=23.5+/−6.6 days; i.t. and i.m. plasmid injection and electroporation (3 treatments) 37.9+/−11.2 days; i.t. plasmid injection and electroporation (2 treatments)=38.1+/−24.5 days; and i.t. plasmid injection and electroporation (3 treatments)=47.8+/−26.1 days. Only two mice, one in the i.t./i.m. group and the other in the i.t. two treatment group were tumor free at 100 days and considered "cured".

B16.F10 melanoma cells will form tumor nodules in the lungs after i.v. injection. Treatment of this model requires a protocol that does not involve a primary or subcutaneous tumor. Therefore, the proposed therapy must induce a systemic immune response that can respond to the tumor burden in the lungs. We showed previously that i.m. injection of IL-12 plasmid followed by electroporation results in high serum levels of IL-12 and IFN-γ. Furthermore, these serum levels could be sustained for a longer period by adding a second treatment four days after the initial treatment.

In this model, C57B1/6 mice i.v. with $1 \times 10^5$ B16.F10 cells was injected and administered i.m. treatment with 50 µg of plasmid encoding IL-12 and electroporation. Four days following the injection and initial treatment, we administered a second treatment. Mice were euthanized 21 days later and their lungs examined for tumor nodules. The table of FIG. 11 shows that 37.5% of mice receiving treatment with IL-12 and electroporation developed lung colonies. Of those three, two mice presented with only one nodule. In contrast, 87.5% of mice not treated developed lung colonies and 75% of mice receiving i.m. injection of plasmid encoding IL-12 without electroporation or mice receiving i.m. injection of a control plasmid with electroporation developed tumor nodules.

To evaluate the efficacy of this treatment on a heavier tumor inoculation, $5 \times 10^5$ B16.F10 cells were injected, i.v. then administered treatments as described above. Because the mice in control groups began dying before 21 days, the data is shown as survival (FIG. 11). 100% of mice in the group receiving i.m. injection of plasmid encoding IL-12 with electroporation survived throughout the experiment. Of the control groups, 62.5% in the no treatment group survived, 75% mice in the injection only group survived, and 50% mice in the group receiving control plasmid followed by electroporation survived. Thus, i.m. injection of plasmid coding for IL-12 followed by electroporation results in the establishment of fewer lung colonies and increases survival of mice with a heavy tumor inoculation.

Figure 13A:
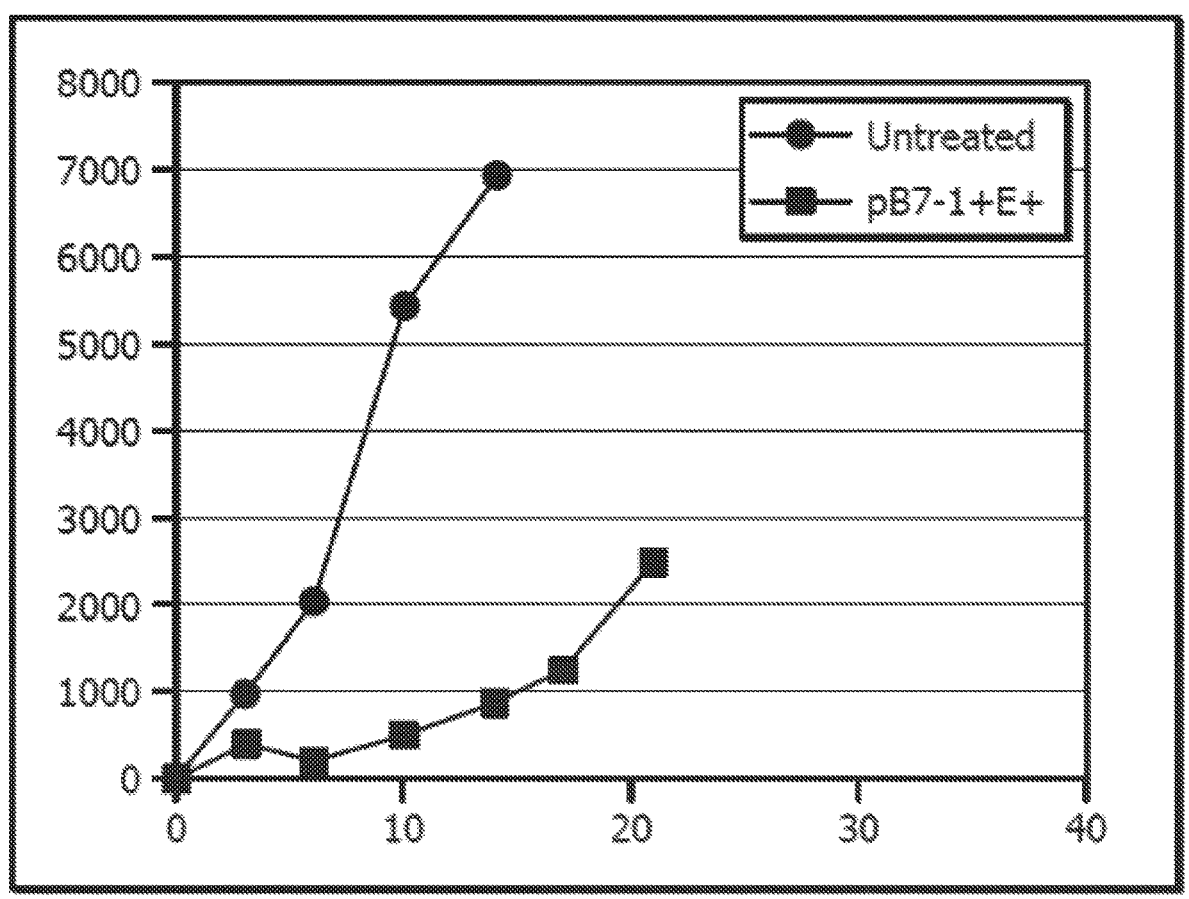
FIG. 13A is a graphical illustration of the results of the treatment of melanoma tumors in a mouse model using B7-1 administered with an electroporation protocol of 1300 V/cm and 100 µs pulses.
Figure 13B:
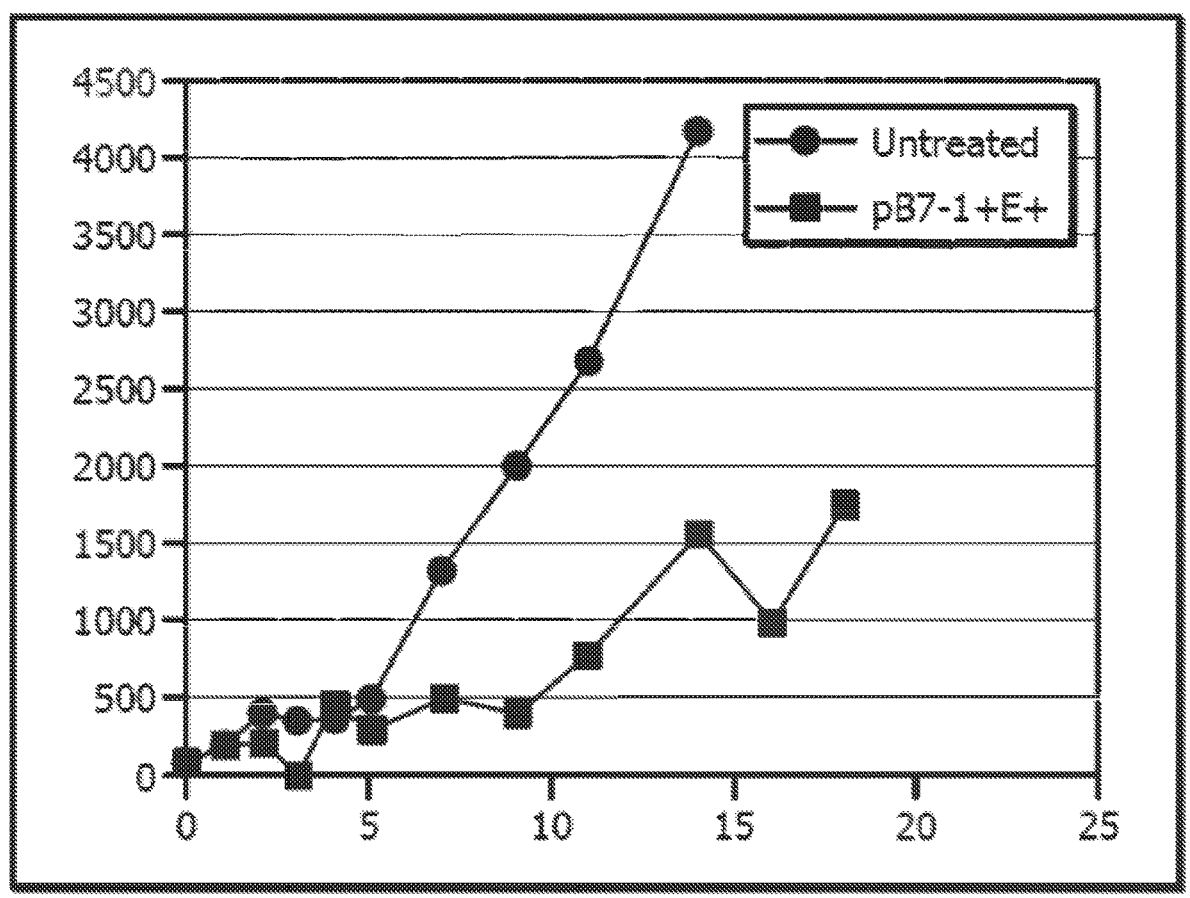
FIG. 13B is a graphical illustration of the results of the treatment of melanoma tumors in a mouse model using B7-1 administered with an electroporation protocol of 1300 V/cm and 100 µs pulses.

With reference to FIG. 13, the results of the treatment of melanoma tumors in a mouse model using plasmid coding for B7-1 followed by electroporation of 1300 V/cm and 100 µs pulses. Similar protocols as previously presented using plasmid coding for IL-12 and IL-15 may be used with plasmid coding for B7-1.

In accordance with the present invention is demonstrated delivery of plasmid encoding IL-12 and B7-1 by electroporation results in successful treatment of subcutaneous tumors as well as lung metastases. We have also shown that this approach is not only effective in treating established tumors but is also effective in preventing the formation of new tumors. The results also suggest that this approach may be useful in treating multiple subcutaneous tumors. There was a reduction in the formation of distant second tumors when only the primary tumor was treated. This effect was seen when the tumor cell injection occurred on the same day of treatment or 4 days prior to treatment. Although administration of other electroporation protocols, using plasmid IL-12 and B7-1, have shown some regression or delay of tumor growth, the treatment protocols presented here have shown the highest rate of success against murine B16.F10 melanoma.

The lack of adverse side effects from the administration of the electrical pulses themselves is an enticing factor for its use. Phase I and II human clinical trials administering electrical pulses for the delivery of chemotherapeutic agents showed success against local tumors. General anesthesia was not required, and the patients did not report any serious adverse events. During the administration of the pulses, patients acknowledged feeling individual pulses but did not report any residual sensation. Thus, the use of electrical pulses is certainly applicable to human use.

Furthermore, for gene therapy studies, electroporation can effectively enhance the delivery of naked DNA. Plasmid DNA does not require cell division, nor has it elicited serious toxicities or immune responses compared to delivery of recombinant protein or the use of viral vectors. As mentioned previously, Lohr et al. compared delivery of IL-12 by electroporation to adenoviruses and found significantly less side effects in the mice following treatment protocols with electroporation. While the use of in vivo electroporation for delivery of plasmid DNA is in a relatively early stage of development, there have been several pre-clinical studies that suggest this approach may be useful against several cancer types. The present invention provides a method for the administration of a plasmid encoding IL-12 and B7-1 with electroporation has a therapeutic effect on primary tumors as well as distant tumors and metastases.

Material and Methods For IL-15

Mice, cell lines and plasmids. The human IL-15 expression plasmid (pIL-15) used was optimized for maximal expression and was 80-fold more efficient than standard pcDNA3-based plasmids. In addition, this human IL-15-expressing plasmid was demonstrated to be approximately 70% homologous to murine IL-15 and was shown to enhance antigen-specific CD8+ immune responses in mice. Also, it has been shown that the human IL-15, generated from the plasmid, did not induce murine anti-human IL-15 antibodies after injection into mice.

In accordance with the present invention, the strategy for plasmid optimization involved the insertion and replacement of the existing Kozak sequence with a stronger Kozak sequence as well as removing upstream inhibitory AUGs through primer design. In addition to these changes, the native long signal peptide sequence was replaced by an optimized leader sequence, which had been shown to enhance secretion and expression of the protein. Subsequently, the optimized IL-15 plasmid was inserted into a cloning vector, which contains a ubiquitous and constitutively active promoter. In the experiments reported here, the optimized IL-15 plasmid has been designated pIL-15. The DNA generated for use in these experiments was produced using endotoxin-free Clontech Giga (Clontech, Palo Alto, Calif.) kits.

In the present invention, C57BL/6 mice, the murine strain syngeneic for the B16F10 melanoma tumor cell line, were used and were purchased from the National Cancer Institute. Mice were housed and maintained during this study in accordance with Association for Assessment and Accreditation of Laboratory Animal Care (AAALAC) guidelines. The B16.F10 murine melanoma cell line clone (CRL 6475) was originally purchased from ATCC and was maintained for studies as monolayers in culture in 90% McCoy's medium supplemented with 10% fetal bovine serum. For the preparation of the single-cell suspension for tumor induction, monolayers of cells were detached from flasks using trypsin-ethylenediaminetetraacetic acid.

Tumor induction and measurement. Tumors were induced by the subcutaneous injection of $10^6$ B16.F10 cells (greater than 90% viability by Trypan blue exclusion) into the left flanks of C57BL/6 mice Tumors were permitted to grow to an average size (i.e. volume) of 40 $mm^3$ before initiation of the treatment regimen. This approximate tumor volume has been determined to be an ideal minimal size for intratumoral injection as the administered treatment volume is retained effectively within the lesion with no significant leakage, providing confidence that the entire dose had been administered. This mean tumor volume for initial therapeutic intratumoral injection has been used in previous studies. Tumor volumes were determined before and at periodic intervals following treatment, using a digital caliper by measuring the longest diameter (a) and the next longest diameter (b) perpendicular to (a). Using these measurements, the tumor volume was calculated by the formula: $V=ab^2\times\pi/6$. The mice were followed in the experiments for 100 days or until tumor volume was determined to be 1300 $mm^3$ at which point any mice had usually succumbed to tumor burden or were requisitely and appropriately euthanized owing to the size of the tumor.

Intratumoral plasmid treatment and in viva electroporation. Female C57BL/6 mice, 6-7 weeks old were injected with the B16.F10 melanoma cells as indicated above and tumors were allowed to grow to the required size. Tumors were then treated intratumorally with either 50 μg of the pIL-15 or the backbone plasmid vector. Subsequently (i.e. within 1 min), tumors from the appropriate groups were subjected to in vivo electroporation using a custom-made applicator, containing six penetrating electrodes that was inserted into the tissue around the tumor and six pulses that were 100 μs long at a field strength of 1500 V/cm were administered using a BTX T820 pulse generator (BTX Harvard Apparatus, Hollister, Mass.) and autoswitcher (Genetronics, San Diego, Calif.).

As indicated, treatments were administered on days 0 and 4 with pIL-15 at a dose of 50 μg. For the treatment, groups P+ or P− indicates with or without treatment with the pIL-15 plasmid and E+ or E− indicates with or without electroporation, respectively. V+ designates the control 'backbone' vector, at a dose of 50 μg, which was delivered with electroporation. The treatment groups were as follows: P−V−E−=no treatment, P−V+E+, P+V−E− and P+V−E+. The results presented are the mean results of a total of 16 mice for each group from two separate experiments.

The mean tumor volumes were calculated for each group at selected time points after the treatment regimen up to day 100 after the initiation of the treatment regimen. Additional quantitative measurements made were fold increase in tumor volume compared to day 0 as well as percent of mice undergoing complete tumor regression coupled with long-term survival.

Expression of intratumoral IL-15 after treatment with pIL-15. In order to access the effect of in vivo electroporation on intratumoral expression of IL-15 after delivery of pIL-15, an enzyme-linked immunosorbent assay (ELISA) assay was utilized. Briefly, three groups of four C57BL6 mice each were injected with $10^6$ B16.F10 cells as described above. The tumors were allowed to develop to the appropriate size (i.e. 40 mm3). One group was untreated, whereas the second and third groups were treated with 50 μg of pIL-15 with or without concomitant in vivo electroporation respectively. Thirty-six hours later, animals were killed and tumors were removed and homogenized by sonication in phosphate-buffered saline containing a protease inhibitor cocktail. The rationale for the 36 hour time point was based upon in vitro expression studies with pIL-15 in other tumor cell lines, which indicated that expression of IL-15 peaked at 36-48 hours. IL-15 levels were then measured in the tumor homogenates/lysates with a human Duo IL-15 kit (R and D Systems Inc., Minneapolis, Minn.) and expressed as specific pg of IL-15/mg tumor. Data indicated are the mean of four quadruplicates. In addition, sera samples were collected from treated mice and assayed for IL-15 expressed from pIL-15.

Histological analysis of sections from pIL-15-treated tumors. An additional study was performed, which examined tumor sections from mice treated with pIL-15. In this study, four groups of mice (n=6) that differed in the treatment regimens (P−V−E−, P+V−E−, P−V−E+ and P+V−E+) were treated on days 0, 4 and 7. Forty-eight hours after the final treatment, the mice were killed after which the tumors were excised, fixed in 10% formalin and sectioned. The sections were stained for histological analysis with hematoxylin and eosin by standard methods and examined microscopically for the presence of tumor cells, necrosis as well as lymphocytic infiltration.

Statistical analysis. Among the different treatment groups, the mean tumor volume was used in the calculation of mean fold increase in tumor volume for the selected time-point assessment as compared to day 0. Statistical analysis of any treatment differences, as measured by mean fold tumor volume increase, was made using Student's t-test methods.

Figure 14:
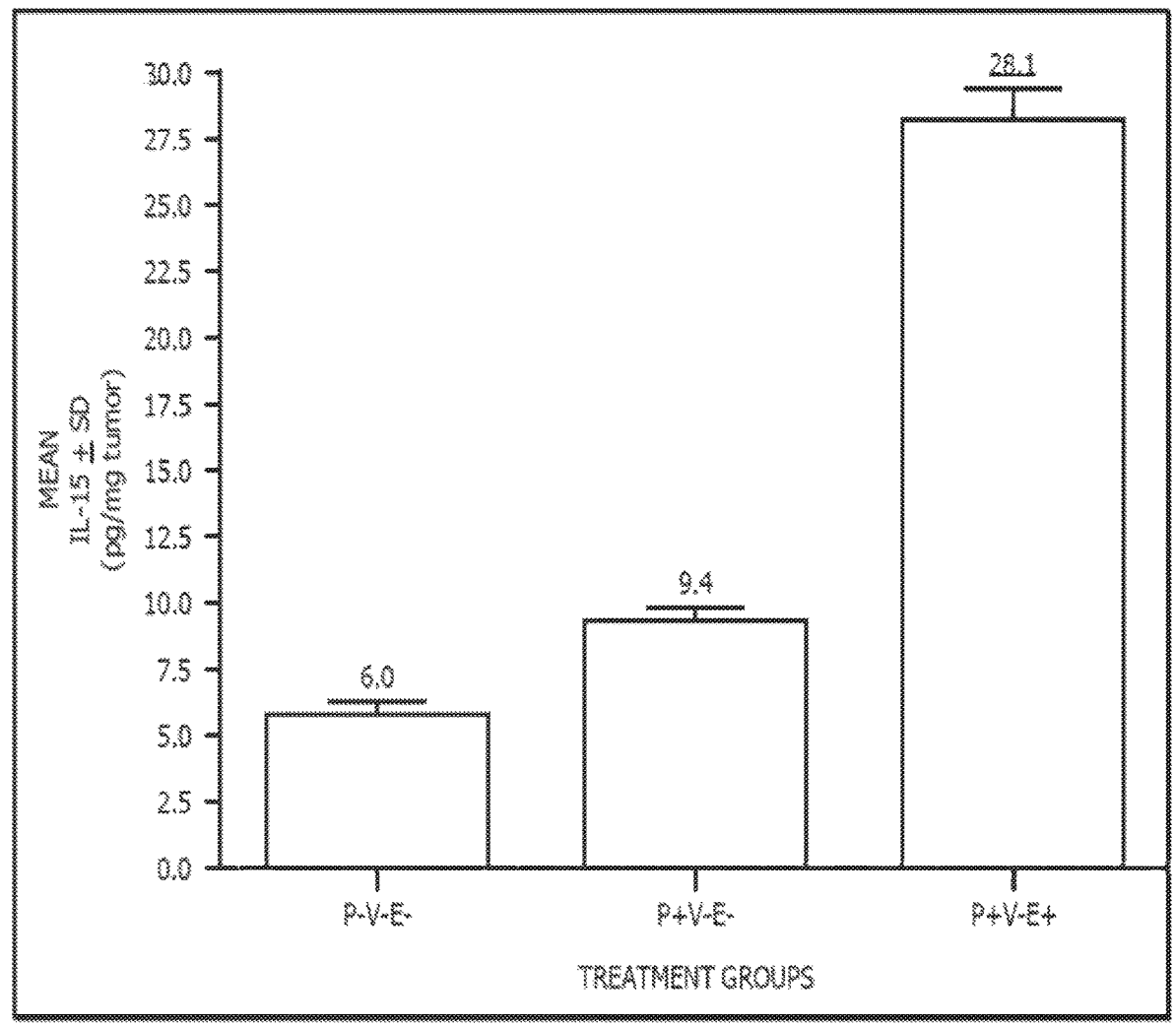
FIG. 14 is a graphical illustration of the measurement of expression of IL-15 in B16 melanoma tumor lysates after intratumoral delivery of pIL-15 with or without electroporation. The mean concentrations of tumoral IL-15 are expressed as pg/mg tumor.

The initial experiment reported here addressed the hypothesis that intratumoral electroporation of subcutaneous B16 melanoma tumors will enhance the expression of IL-15 from an IL-15 DNA expression plasmid. As indicated above, 50 µg of the pIL-15 was injected intratumorally into subcutaneous B16.F10 melanoma tumors of the appropriate tumor volume in either the absence (P+V–E–) or presence (P+V–E+) of subsequent intratumoral electroporation. Thirty-six hours later, tumors were excised and homogenized and IL-15 concentrations were measured and expressed as pg IL-15/mg tumor. The background IL-15 concentration in tumor homogenates of untreated (i.e. no pIL-15 or electroporation) was 6.0 pg IL-15/mg tumor. FIG. 14 shows intratumoral IL-15 concentrations of 9.4 and 28.1 pg/mg tumor in the P+V–E– and P+V–E+ groups, respectively. This result indicates that in vivo electroporation enhanced intratumoral expression of IL-15 approximately 4.7-fold, compared to non-treated controls, and threefold compared to pIL-15 treatment without electroporation. In this invention, the levels of IL-15 measured in both the P+V–E– and P+V–E+ groups were statistically elevated ($P<0.05$ by the Students t-test) when compared to the level measured in the P–V–E– group. Also, and importantly, the intratumoral IL-15 level measured in the P+V–E+ group was significantly elevated compared to that measured in the P+V–E– group. These results demonstrate the ability of the pIL-15 plasmid to be expressed within the tumor after intratumoral delivery with additional significant enhancement of expression through delivery by in vivo electroporation. However, at this 36 h post-treatment time point, IL-15 expressed from this plasmid was not measurable in sera samples from mice from the appropriate treatment groups (data not shown).

It was subsequently relevant to determine the potential therapeutic efficacy of intratumoral delivery of pIL-15 and whether in vivo electroporation could enhance any antitumor therapeutic effect of pIL-15. Therapeutic end points in these experiments are 'slowing' of tumor growth, as measured by tumor volume, as well as by the incidence of complete regressions of tumors coupled with the long-term survival. In this experiment, C57BL/6 mice were injected subcutaneously with B16.F10 melanoma cells. When tumors had attained the appropriate volume mice were separated into four groups (n=16 each) and treated. In untreated controls, the tumors grew rapidly, which is characteristic of the B16.F10 clone, and all of the tumors reached a volume of approximately 1000 mm$^3$ by day 18.

As shown in the table of FIG. 15, data for the other groups at day 18 after the initiation of treatment are summarized. The day 18 measurement was selected because at this time point at least 50% of the mice in each of the treatment groups were still alive (i.e. had not succumbed to tumor burden) allowing for a meaningful analysis. The untreated control (P–V–E–), as indicated above, had undergone an average 22-fold increase (i.e. from 46.5 to 1026.8 mm3) in tumor volume at day 18 compared to day 0. By contrast, in the P+V–E+ group, the mean fold tumor volume increase from day 0 to day 18 was only 1.2 (i.e. from 39.9 to 49.6 mm3).

In addition to these findings, there appeared to be some tumor growth slowing/attenuation effect in the other treatment groups as well at day 18 compared to day 0. That is, the fold increase in tumor volume from day 0 to day 18 in groups P–V+E+ P–V+E+ and P+V–E– was 12.1, 4.2 and 15.6, respectively. These results indicate an initial 'nonspecific' vector backbone and electroporation effect on tumor growth. However, the growth attenuation effect in the P+V–E+ group, receiving the IL-15 expressing plasmid, was significantly greater in terms of fold increase in tumor volume, compared to any of the other treatment groups when accessed by a Student's t-test ($P<0.05$). The growth attenuation effect noted with control vector treatment or electroporation alone has been noted previously and has been attributed to effects of CpG motifs within the vector and an initial inflammatory/toxic effect of the electroporation. It is relevant to point out, however, that at day 18 the percent of mice in the P+V–E+ group, which had undergone tumor regression, was significantly higher (i.e. 62.5%) than any of the other treatment groups.

Figure 16:
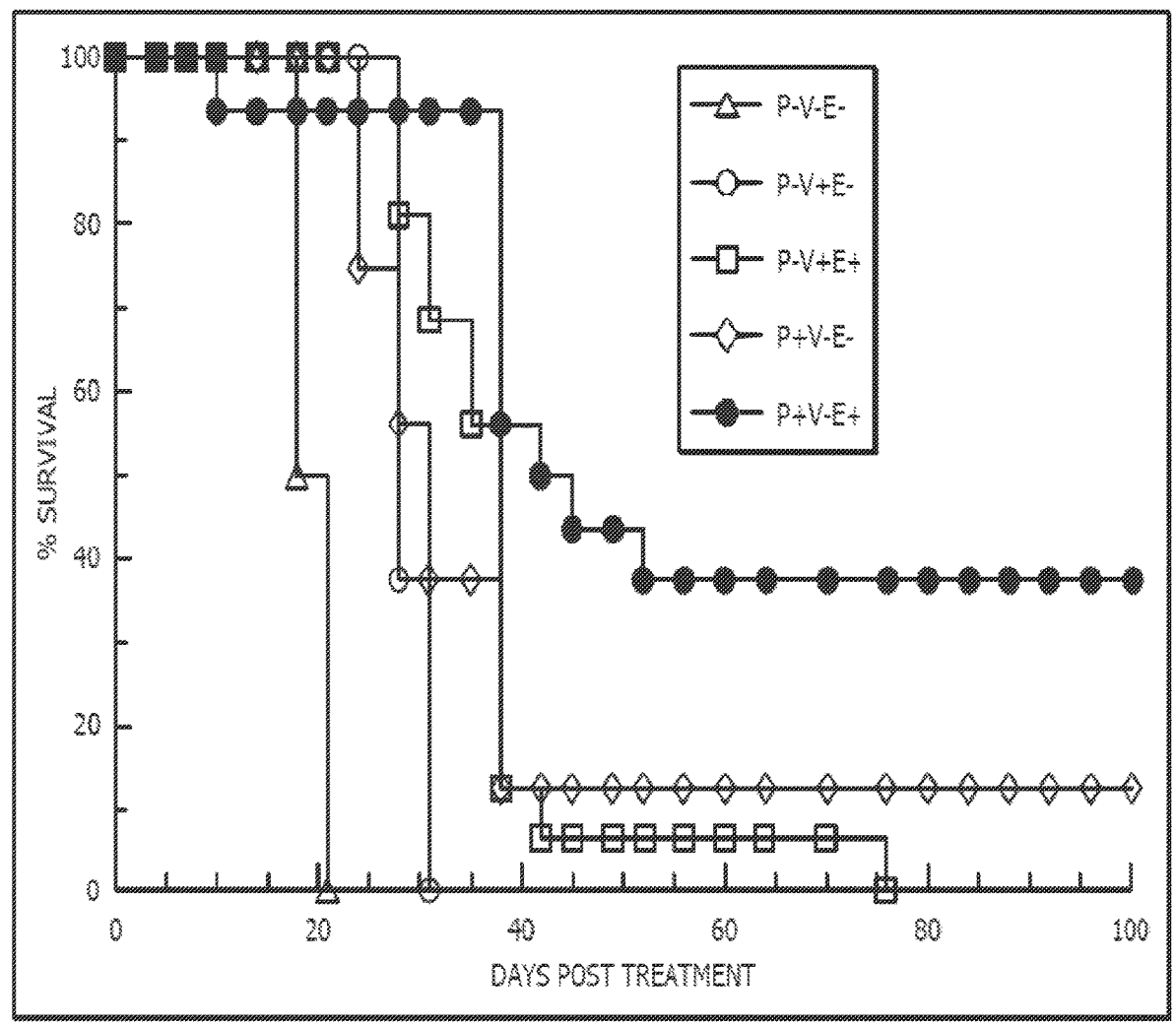
FIG. 16 is a graphical illustration of Kaplan-Meier survival curves for C57BL/6 mice in treatment groups injected with pIL-15 or control plasmid with or without electroporation.

Ultimately, the endpoint for this study with the most relevant clinical significance is complete tumor regression coupled with long-term survival of the mice. Time-point measurements of percent mouse survival with complete tumor regression within the different treatment groups were performed up to 100 days after the initiation of the experiment. For the B16.F10 murine melanoma tumor model, complete tumor regression and animal survival 100 days post-rumor cell injection has been generally accepted as the benchmark for 'curative' therapeutic regimens. That is, maintenance of complete tumor regression 100 days after the initiation of treatment can be considered to be a long-term 'cure'. These data are summarized in the Kaplan-Meier survival curves shown in FIG. 16. The data summarized in the graph indicates that at the day 100 time point only the P+V–E– and P+V–E+ treatment groups had surviving animals with complete tumor regressions. Mice in all of the other groups had succumbed to tumor burden by that time point. In the P+V–E– group, 2/16 (12.5%) of the mice survived until at least the day 100 measurement. In contrast, the P+V–E+ group had 6/16 (37.5%) of the treated animals surviving to at least day 100. This was a threefold enhancement of the therapeutic effect compared to pIL-15 treatment without electroporation. This enhancement was statistically significant at the 0.05 level when measured by a Student's t-test. Importantly, in the control groups that were treated with the vector backbone with or without electroporation, none of the animals survived long term with complete tumor regressions. In addition, no tumor-bearing mice that received electroporation alone (data not shown) survived long term with complete tumor regression. These results demonstrated that the pIL-15 treatment was able to mediate complete tumor regression/long-term survival in B16 melanoma bearing C57BL/16 mice. Also, the end point therapeutic effect of pIL-15 was also enhanced by electroporation, indicating the clinical potential of this delivery method.

As indicated in the Materials and Methods section, an additional study was performed, which examined tumor sections from the various groups histologically 48 h after the final treatment. This was carried out in order to access for the presence of melanoma tumor cells. Results of the histological analysis indicated that in the P–V–E– control group there was evidence of tumor in all of the mice, whereas in the P+V–E+ group 83% of the mice failed to demonstrate histologic evidence of melanoma. In the P–V+E+ and P+V–E– groups, only 17% of the mice in each group failed to demonstrate evidence of tumor. These data further establish the therapeutic efficacy of treatment with pIL-15 and in vivo electroporation.

An extension of the regression/long-term survival study reported here was performed in which long-term survivors were challenged subcutaneously with $10^6$ B16.F10 melanoma cells. This experiment was conducted in order to determine whether mice cured of their initial tumors through treatment could resist re-challenge with the B16.F10 cell line. Resistance to re-challenge would likely assume that an immunological mechanism (e.g. T-cell immune response) was operant and which putatively could be involved in protection. In this study, surviving mice from the study described in FIG. 16 were 'challenged' shortly after the day 100 time point with the melanoma cells and were accessed over time for the development of tumors. The results demonstrated that 60% of mice re-challenged from the P+V−E+ group remained tumor free for at least 50 days, whereas likewise one of the two mice (i.e. 50%) from the P+V−E− group failed to develop a tumor in this time span. The results from this limited re-challenge study, while not statistically significant, can be considered to be biologically significant because of the aggressive nature of the B16.F10 melanoma cell line. That is, naive mice injected with the number of B16.F10 melanoma cells used in these experiments would normally succumb to tumor burden within approximately 20 days. As such, these findings suggested that pIL-15 treatment mediated an immunological response that protected a proportion of the surviving/cured mice from tumor re-challenge.

The present invention demonstrates the therapeutic antitumor potential of the IL-15-expressing plasmid when delivered intratumorally into established subcutaneous B16 melanoma tumors in CS7BL/6 mice. In addition, it was also demonstrated that delivery of pIL-15 with in vivo electroporation significantly enhanced the antitumor activity of this expression plasmid, which was associated with an approximate threefold and 4.7-fold increase in expression of IL-15 when delivered with electroporation as compared to treatment without electroporation or no treatment, respectively. Also, it appeared that the plasmid backbone vector, when delivered by electroporation resulted in an initial temporary attenuation of tumor growth due likely owing to immune stimulatory effects of the CpG motifs contained in the plasmid as well as an inflammatory response from the electroporation procedure. However, only treatment with pIL-15 resulted in any complete tumor regressions with long-term survival, indicating specificity in mediating this relevant endpoint therapeutic response. It is anticipated that further studies with electroporative delivery of pIL-15 will allow maximization (i.e. at least an 80% complete tumor regression/long-term survival rate) of the therapeutic response. Therapeutic maximization strategies include modulation of the dose as well as the number and intervals of treatments.

Re-challenge with B16 melanoma cells of mice that had been 'cured' of the initial melanoma tumors by treatment with pIL-15 plus electroporation resulted in resistance to tumor challenge in a large proportion of the mice. This suggested that a mechanism resulting in immunological memory mediated the resistance to tumor cell challenge even though preliminary analysis at the 36 h post-treatment time point failed to demonstrate sera levels of expressed IL-15. Future studies in this area will be aimed at further examining the tumoral and sera IL-15 expression levels after treatment with pIL-15 plus electroporation as well as the measurement of antigen-specific memory T cells or NK cell activity as possible immunological mechanisms for mediating the antitumor activity of pIL-15.

The tumor induction and challenge model utilizing the B16.F10 cell line, as reported in this invention disclosure, is particularly relevant for several reasons: (a) the B16.F10 melanoma is a highly invasive, metastatic and poorly immunogenic tumor, which is very difficult to 'cure', (b) the treatment regimen used in this study was administered to established tumors rather than injected concomitantly with tumor cells or before malignant lesions had visibly formed and (c) the ultimate therapeutic end point was complete tumor regression and long-term survival rather than simply attenuation of tumor growth. This is relevant as the majority of other studies with this tumor cell line have either administered treatments before the development of visible tumors or accessed tumor growth attenuation as the therapeutic end point.

As such, in accordance with the present invention, the potential utility of naked DNA plasmids expressing therapeutic cytokines such as IL-15 as anticancer therapeutics has been described. In addition, the enhancement of the delivery, expression and therapeutic index for these molecular reagents through intratumoral electroporation has been established.

It will be seen that the objects set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described.

What is claimed is:

1. A method of treating cancer in a subject comprising: injecting a cancerous tumor in the subject with an effective dose of plasmid coding for an immune stimulatory interleukin; and administering electroporation therapy to the tumor, the electroporation therapy comprising the administration of at least one pulse having a field strength of at least 400V/cm and a duration of less than 1 millisecond resulting in the regression of the tumor, wherein the electroporation therapy comprises six pulses.

2. The method of claim 1, wherein the immune-stimulatory interleukin is a heterodimeric interleukin.

3. The method of claim 2, wherein the plasmid encoded subunits of the dimeric interleukin are joined by an internal ribosomal entry site (IRES).

4. The method of claim 3, wherein the plasmid encodes an IL-12 p40 subunit.

5. The method of claim 1, wherein the method further reduces formation of new tumors.

6. The method of claim 1, wherein the method further results in regression of at least one distant tumor.

7. The method of claim 1, wherein regression of the tumor results in increased survival of the subject.

8. The method of claim 1, wherein proliferation of T-cell lymphocytes is increased.

9. The method of claim 8, wherein the T-cell lymphocytes are CD4+ T-cells, CD8+ T cells, and/or natural killer cells.

10. The method of claim 1, wherein infiltration of lymphocytes in the tumor is increased.

11. The method of claim 10, wherein the lymphocytes include CD4+ T-cells, CD8+ T cells, and/or natural killer cells.

12. The method of claim 1, wherein IFNγ expression in the tumor is increased.

13. The method of claim 1, wherein the at least one pulse has a field strength of about 700V/cm.

14. The method of claim 1, wherein the at least one pulse has a duration of about 100 μsec.

15. The method of claim 1, wherein the cancer is melanoma, Merkel cell carcinoma, T-cell lymphoma, squamous cell carcinoma, pancreatic cancer, hepatocellular carcinoma, adenocarcinoma, breast cancer, squamous cell, or lung cancer.

16. The method of claim 1, wherein the method further comprises a second treatment comprising injecting the tumor with an effective dose of plasmid coding an immune stimulatory interleukin; and administering electroporation therapy to the cancerous tumor, the electroporation therapy comprising the administration of at least one pulse having a field strength of at least 400V/cm and a duration of less than 1 millisecond, wherein the second treatment is administered after a first treatment.

17. The method of claim 16, wherein the second treatment is administered 4-7 days after the first treatment.

18. The method of claim 17, wherein the method further comprises a third treatment comprising injecting the tumor with an effective dose of plasmid coding for an immune stimulatory interleukin; and administering electroporation therapy to the cancerous tumor, the electroporation therapy comprising the administration of at least one pulse having a field strength of at least 400V/cm and a duration of less than 1 millisecond, wherein the third treatment is administered after the second treatment.

19. The method of claim 18, wherein the second treatment is administered about 4 days after the first treatment and the third treatment is administered about 3 days after the second treatment.

20. A method of increasing infiltration of lymphocytes to at least one tumor comprising: injecting the at least one tumor with an effective dose of at least one plasmid coding for an immune stimulatory interleukin; and administering electroporation therapy to the tumor, the electroporation therapy comprising the administration of at least one pulse having a field strength of at least 400V/cm and a duration of less than 1 millisecond resulting in increased infiltration of the T-cell lymphocytes to the at least one tumor, wherein the electroporation therapy comprises no more than six pulses.

21. A method of reducing angiogenesis in at least one tumor comprising: injecting the at least one tumor with an effective dose of at least one plasmid coding for IL-12; and administering electroporation therapy to the tumor, the electroporation therapy comprising the administration of at least one pulse having a field strength of at least 400V/cm and a duration of less than 1 millisecond resulting in reduction of angiogenesis in the at least one tumor, wherein the electroporation therapy comprises no more than six pulses.

* * * * *